(12) United States Patent
Van Duren et al.

(10) Patent No.: US 7,338,515 B2
(45) Date of Patent: Mar. 4, 2008

(54) SYSTEM, COMBINATION AND METHOD FOR CONTROLLING AIRFLOW IN CONVECTIVE TREATMENT

(75) Inventors: Albert Philip Van Duren, Chaska, MN (US); Allen Hamid Ziaimehr, Arden Hills, MN (US); John Paul Rock, Minneapolis, MN (US); Scott Douglas Augustine, Bloomington, MN (US); Gary Rabindranath Maharaj, Eden Prairie, MN (US); Randall Charles Arnold, Minnetonka, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 1534 days.

(21) Appl. No.: 10/131,068

(22) Filed: Apr. 23, 2002

(65) Prior Publication Data

US 2003/0036786 A1    Feb. 20, 2003

Related U.S. Application Data

(60) Continuation-in-part of application No. 10/024,387, filed on Dec. 17, 2001, now Pat. No. 7,220,273, which is a division of application No. 09/546,078, filed on Apr. 10, 2000, now Pat. No. 6,447,538.

(51) Int. Cl.
*A61F 7/00* (2006.01)
(52) U.S. Cl. .................................................. 607/96
(58) Field of Classification Search ............ 607/96–98, 607/1, 104, 107–108, 112, 114; 606/27; 5/423; 219/212
See application file for complete search history.

(56) References Cited

U.S. PATENT DOCUMENTS

| | | | |
|---|---|---|---|
| 5,159,981 A | 11/1992 | Le | ............................ 166/325 |
| 5,230,611 A * | 7/1993 | Shelton | ........................ 417/437 |
| 5,318,568 A | 6/1994 | Kaufmann et al. | ............ 607/107 |

(Continued)

OTHER PUBLICATIONS

EN-60601-2-35-1996 E: European Standard for medical electrical equipment, heating blankets, heating pads, heating mattresses, safety requirements, protection against electric shock, protection against mechanical hazard, radiation protection, fire protection, environmental conditions adopted by CENELEC, European Committee for Electrotechnical Standardization.

*Primary Examiner*—Roy D. Gibson
*Assistant Examiner*—Pete Vrettakos
(74) *Attorney, Agent, or Firm*—Incaplaw; Terrance A. Meador

(57) ABSTRACT

In a convective system that includes a blower to thermally treat and pressurize air, a convective device to receive and convect the thermally-treated pressurized air, and an air hose to conduct a flow of thermally-treated pressurized air from the blower to an inlet port in the convective device, an interface device is provided to control the flow of air at the interface where the inlet port and an end of the air hose operate to conduct the flow of air out of the air hose into the convective device. The interface device is received at the end of the air hose and operates to support the flow of air out of the end when the end and the inlet port are brought together. The interface device operates to stop, inhibit, or restrict the flow of air out of the end when the end and the inlet port are separated.

13 Claims, 15 Drawing Sheets

U.S. PATENT DOCUMENTS 6,357,491 B1   3/2002   Buchanan et al.
6,447,538 B1   9/2002   Van Duren et al. ........... 607/96
6,493,889 B2   12/2002  Kocurek ........................ 5/423

* cited by examiner

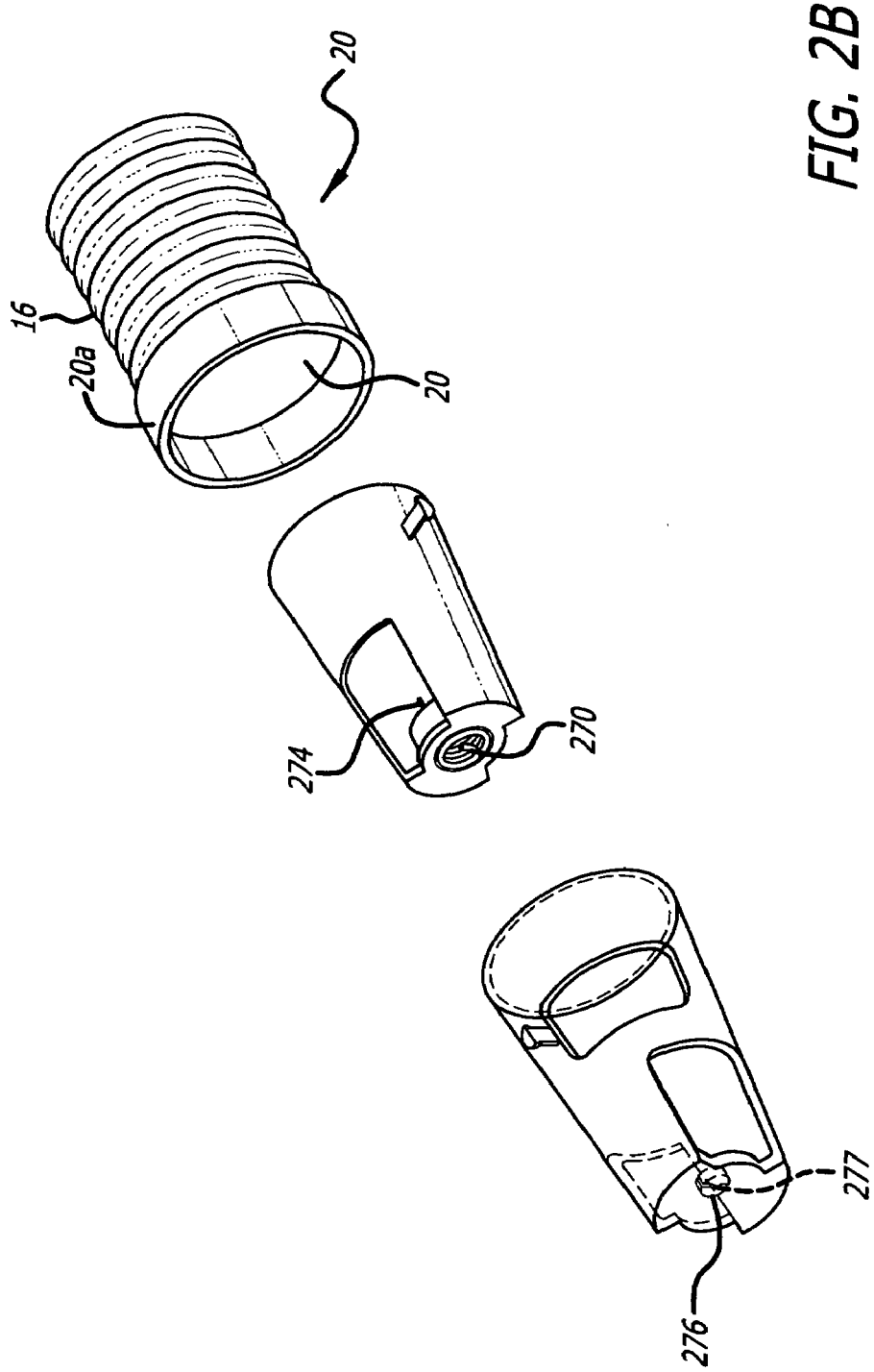

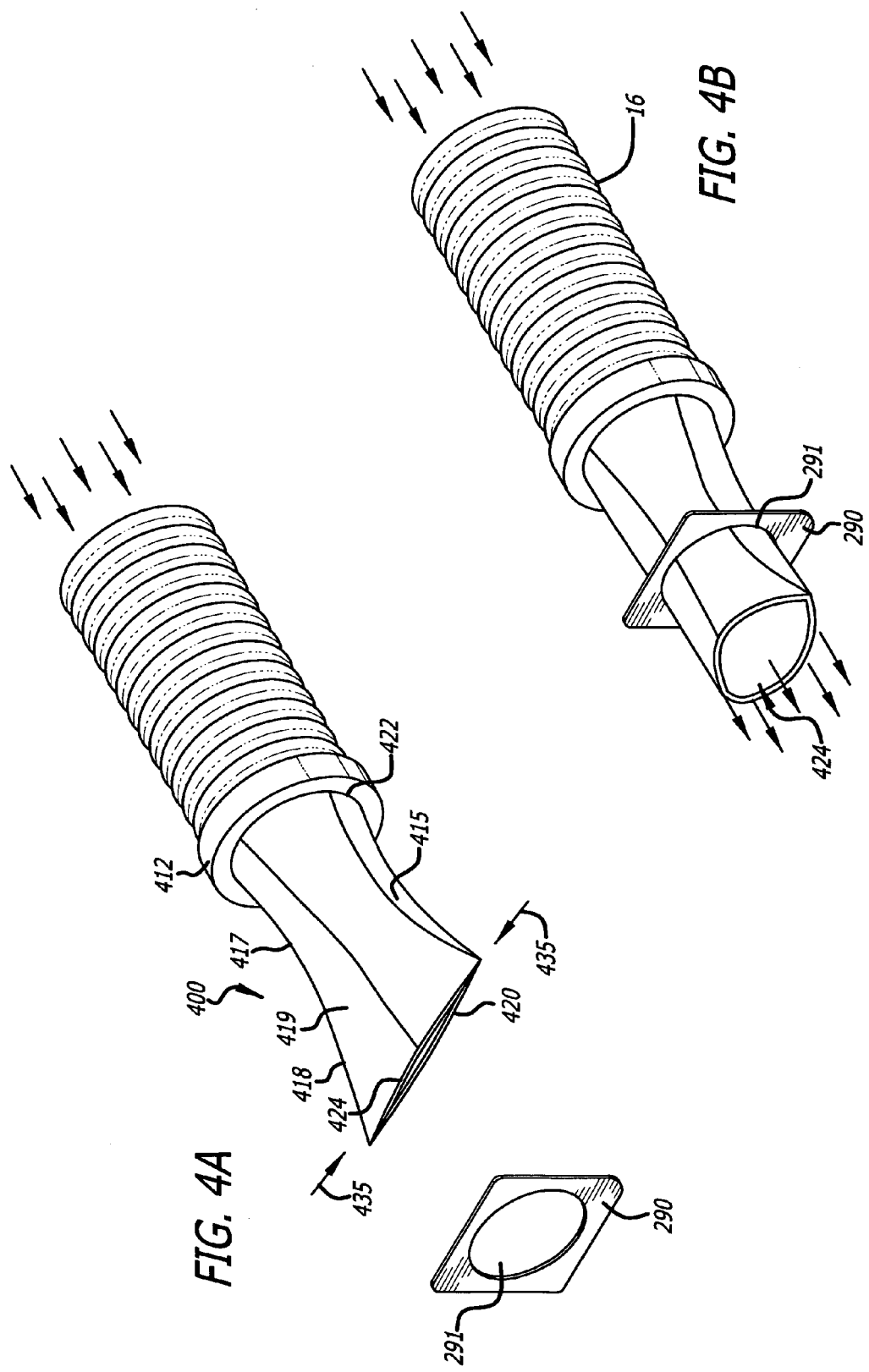

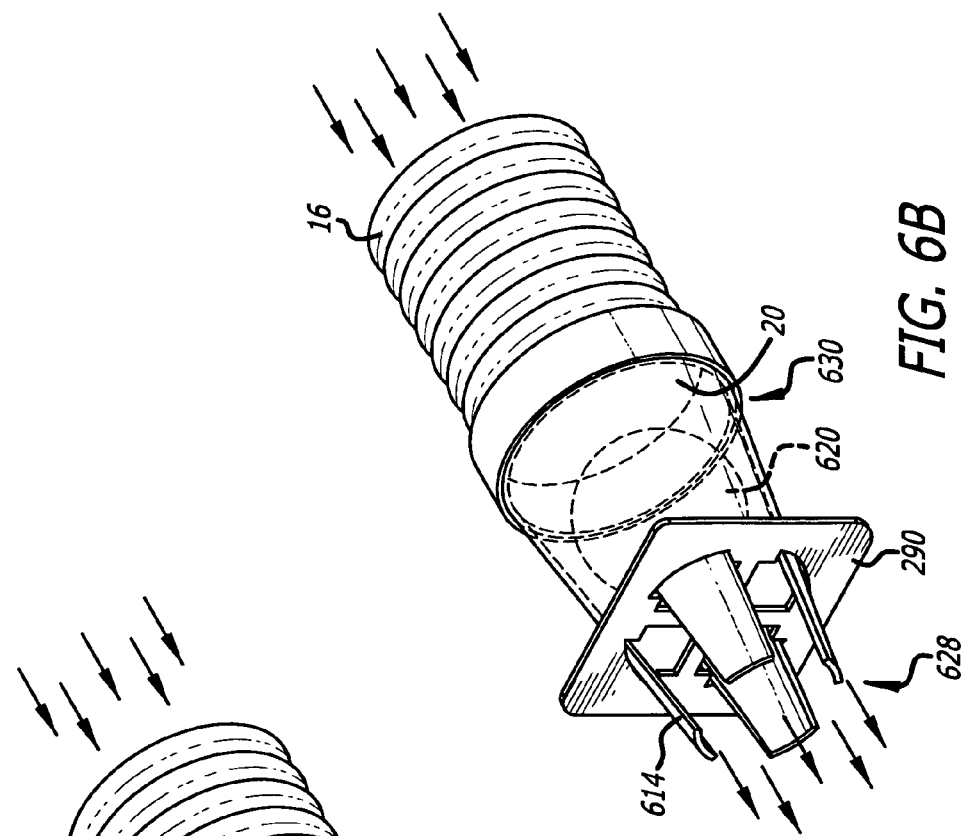
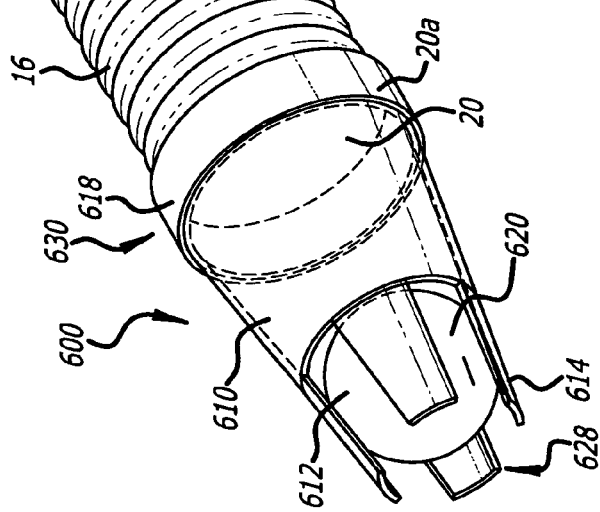
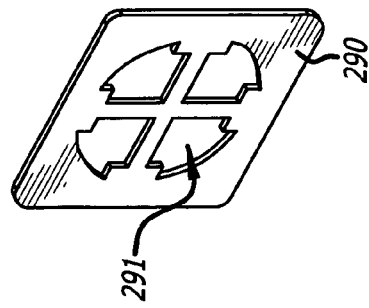
FIG. 6A
FIG. 6B

SYSTEM, COMBINATION AND METHOD FOR CONTROLLING AIRFLOW IN CONVECTIVE TREATMENT

PRIORITY AND RELATED APPLICATIONS

Priority is claimed as a continuation-in-part of U.S. patent application Ser. No. 10/024,387, filed Dec. 17, 2001, now U.S. Pat. No. 7,220,273, which is incorporated herein by this reference.

U.S. patent application Ser. No. 10/024,387 claims priority as a divisional of U.S. patent application Ser. No. 09/546,078 filed Apr. 10, 2000, now U.S. Pat. No. 6,447,538.

This application contains subject matter related to the subject matter of U.S. patent application Ser. No. 09/138,774 filed Aug. 24, 1998, now U.S. Pat. No. 6,126,681, and to its continuation-in-part, U.S. patent application Ser. No. 09/546,078, filed Apr. 10, 2000, now U.S. Pat. No. 6,447,538. Both of these patent documents are incorporated herein by this reference.

FIELD OF THE INVENTION

This invention relates generally to forced-air convection treatment of persons and, more particularly, to a system, a combination, and a method for controlling airflow in convective treatment in order to prevent injury to a person such as might occur when thermally-conditioned (heated or cooled) air is discharged directly onto the person.

BACKGROUND OF THE INVENTION

A convective treatment system consists of a temperature-control/blower unit (known simply as a "blower"), a ducting system, a convective device such as a convective warming blanket, and/or an infusate heat exchanger. A blower aspirates air from an ambient environment, changes its temperature to a desired value, pressurizes the air above the ambient pressure, and discharges the air at an exhaust port. U.S. Pat. No. 6,126,393 describes such a blower and associated temperature and noise control schemes. In an exemplary convective treatment system, pressurized, thermally regulated air produced by a blower is conveyed through a ducting system and delivered to a convective device, such as a convective warming blanket, that distributes the thermally regulated air around a person or a specific body area of a person. A person can be a human being, animal, or thing. In some applications, a blower unit may be used to operate other accessory devices with or without an convective device. In these stand-alone applications, the blower unit may be used to warm infusates, such as blood or saline, through the use of a heat exchanger adapted to fit within the duct system. U.S. Pat. No. 5,807,332 describes one type of nonconvective device that is used to warm infusates for administration into persons. The use of an infusate warmer does not preclude the concomitant use of a convective device; however, the distal end of the air supply duct is covered with an air diffuser during the exclusive use of an infusate warmer. The user must intentionally place the diffuser over the distal end of the air supply duct. The diffuser allows the heated air to escape from the distal end of the air supply duct but prevents the heated air from striking the patient directly.

A convective device may be embodied, for example, in an inflatable device which inflates with pressurized, thermally regulated air and has one or more surfaces adapted for expelling air onto a person. Such devices may lie on, around, or under the person. A convective device is generally realized as a blanket, but can be embodied by other appliances or attachments that are designed to be operated by or with the application of pressurized, thermally conditioned air. When used herein, the term "convective device" is intended to include all blankets, pads, covers, manifolds, and equivalent structures that operate as just described. Irrespective of orientation, a convective device utilized for convective thermal treatment of persons performs at least three basic functions. These functions are 1) the conveyance of thermally conditioned air from at least one inlet port into the device, 2) the imposition of a heat gain or loss that changes the temperature of the thermally conditioned air, and 3) the extravasation of the thermally conditioned air from the device. In the following discussion, the assumption is that such a convective treatment device is operated to warm a person by delivery of heat to the person.

In those convective treatment systems which warm a person by the application of heat, heat may be transferred by convection, radiation, and conduction, but convection generally predominates at the interface between the convective device and the person. The rate of convective heat transfer depends on material properties, surface boundary conditions, and significantly, fluid velocity.

Heat is lost from a convective treatment system whenever a temperature gradient exists between it and the ambient environment. During normal operation of the system, the temperature of the air expelled onto the person is maintained at a level that is generally higher than the person's skin surface temperature, but not high enough to cause tissue damage. In order to counter the loss of heat from the system, however, the air is heated initially to a temperature that may exceed the thermal damage threshold at the target site on the person's skin. Within certain limits, the amount of heat lost from the system is predictable. This predictability allows the system to operate safely by measuring and controlling the temperature at the proximal end of the air supply duct that connects the blower to the convective device. If any factors upon which the assumption of predictability depends are altered, however, the fluid temperature at the distal end of the duct system may be affected.

Several intrinsic and extrinsic factors contribute to the rate of heat loss from a convective treatment system. Among the intrinsic factors are the surface area and material characteristics of the duct and convective device, and the residence time of the warmed air within the duct and convective device. Extrinsic factors include, but are not limited to, ambient temperature and air velocity in the area immediately adjacent to the duct and the convective device. The residence time of the heated fluid within the system is a function of its pressure and the resistance exerted by the entire system. Factors that influence resistance are the duct diameter and length, the orientation of the duct, and the resistance of the convective device or devices.

One hazard associated with the use of convective treatment is burns. First-, second-, and third-degree burns have occurred through the improper use of convective treatment systems. The burn hazard is accentuated by the intentional or accidental alteration of the intrinsic or extrinsic factors that moderate the heat loss in the system. The alteration of any of these factors introduces an unpredictable amount of heat loss into the system, which can significantly alter the temperature or velocity of the heated air delivered to the person. One of the more important factors that influence the temperature of warm air flowing out of the air supply duct through the end where it connects to the convective device is the residence time of the air within the duct. The end through which air flows out of the air supply duct is usually referred to as the "distal end" of the air supply duct. Typically, a nozzle may be mounted to this end. The temperature of pressurized warm air exiting the duct at this end is called "nozzle temperature" (whether or not a nozzle is mounted thereto). In general, a decrease in residence time of the pressurized warmed air is usually associated with an increase in the nozzle temperature of the air.

In the field, a common misuse of one or more components of a convective treatment system occurs. Either intentionally or accidentally, some users fail to connect the convective device to the distal end of the duct and allow the heated air discharged from the distal end to make direct contact with the person. In view of the fact that an air supply duct is typically embodied as an air hose, this practice has come to be known as "hosing" or "free-hosing." In other cases, operators have failed to connect the convective device to the duct and allowed the heated duct to make direct contact with the person's skin. Users who have experienced therapeutic misadventures through this type of misuse have reported their experiences of thermal injuries to the FDA and the manufacturers of the offending convective treatment systems. Some manufacturers of have responded by warning and training users and affixing labels to the thermal-control/blower units and convective devices. Despite warnings, training, and labeling, however, persons continue to be injured through misuse of warning devices.

The American Society for Testing and Materials (ASTM) has recently circulated a draft standard (ASTM F29.19.01) from the Subcommittee for Patient Warming Equipment entitled Standard Specification for Circulating Liquid and Forced Air Patient Temperature Management Devices. The members of the ASTM subcommittee recognized the hazards associated with the practice of free-hosing and developed requirements for equipment to limit skin surface temperatures to 48° C., or less, during any operating or fault condition. Additionally, the standard requires the manufacturers of thermal-control/blower units to affix a cautionary statement to the distal end of the air supply duct that warns the user against the practice of "free-hosing." Thus, the ASTM standard explicitly recognizes the importance of air temperature, and tacitly acknowledges the role of airflow, in causing thermal burns.

Hosing causes at least four uniquely hazardous conditions to exist: 1) The loss of the resistance from the lack of an convective device leads to a decrease in the residence time of warmed air in the air supply duct. As the warmed air has less time to cool in the air supply duct, it arrives at the distal end of the duct at a higher than normal temperature; 2) The lack of airflow resistance from the absence of the convective device also leads to an increase in the air velocity that is exhausted from the supply duct; The relative increase in air velocity can lead to significantly higher heat transfer rates if the air strikes the skin; 3) The lack of an convective device makes it possible for the high temperature and high velocity air to strike directly the person's skin over a very small area. In essence, all, or most, of the heat energy intended to be distributed over a large surface area is concentrated onto a very small area; and 4) The lack of an convective device makes it possible for the air supply duct itself to make direct contact with the person's skin.

It is manifest that the hazards of hosing are not intentionally visited on any victim. Nevertheless, it is the case that large caseloads and near-crisis conditions can distract the attention of those who are in charge of the immediate operation of convective treatment systems. In such circumstances, the practitioner may be unaware of the development of conditions that pose a hazard of burns, or may be forgetful of known conditions that require close and constant attention. Accordingly, significant benefits would be realized by safety provisions that operate automatically to reduce the risk of harm that can arise during the operation of convective treatment systems. Especially desirable are measures that would automatically mitigate the potential of burns that might occur when the air supply duct is separated from the convective device in a convective treatment system that delivers warmed air for treatment.

The assignee of this application has designed safety provisions that reduce the risk of burns by modulating the operation of a blower in response to changes in the integrity of the connection between the air duct and the convective device. These provisions are set out in U.S. Pat. No. 6,128,681 and a continuation-In-part thereof, U.S. patent application Ser. No. 09/546,078, now U.S. Pat. No. 6,447,538both of which are Incorporated herein by this reference. However, these provisions must be implemented in the structure and operation of a blower, and Implicate redesign and reconstruction of exiting blower architecture Accordingly, there is an immediate need for additional, easily-implemented measures in convective treatment technology to 1) automatically mitigate a potentially unsafe condition irrespective of an operator's awareness of the unsafe condition, 2) prevent the intentional or unintentional misuse of convective treatment system components by users who fail to connect the appropriate convective devices to the distal end of the air supply duct and thereby allow heated air to make direct contact to the person, and 3) prevent the air supply duct from causing thermal injury to the person if it makes direct contact with the person's skin.

SUMMARY OF INVENTION

It is an object of this invention to automatically correct the condition where an air supply duct that is still conducting pressurized air is not connected to a convective device.

A further object of this invention is to correct the condition in a way that does not interfere with the normal operation of a convective device or an accessory device whenever these devices are properly attached to the air supply duct.

The invention is based on the critical realization that the there exists an interface in a convective treatment system where measures can be implemented to reduce, if not stop, the flow of heated air when the air supply duct is disconnected, uncoupled, or detached from the convective device. The interface is where the connection, coupling, or attachment of the air supply duct with the convective device is made. At this interface, an interface device is provided that reduces, restricts or stops the flow of air through the end when the end is disconnected, uncoupled, or detached from the convective device. The interface device may be manually operated or self-actuating.

BRIEF DESCRIPTION OF THE DRAWINGS

FIG. 1B is a magnified partial perspective view of a portion of a convective device where an inlet port is located, with an end of an airhose positioned to e received in the inlet port.

FIGS. 2A-2E illustrate an embodiment of an interface device according to the invention.

FIGS. 4A and 4B illustrate another embodiment of an interface device according to the invention.

FIGS. 6A and 6B illustrate another embodiment of an interface device according to the invention.

DETAILED DESCRIPTION OF THE EMBODIMENTS

In this description, a convective warming system will be described, together with certain elements of such a system. The elements will be denominated by terms that are selected for syntactic convenience and utility in suggesting a structure or a function. The terms are not selected, nor are they intended, to constrain or limit the range of structural and functional equivalents to which the elements, alone or in combination, are entitled.

In this regard, the terms "blower" and "convective device" are defined above. The term "air supply duct" is used in the background to denote a tubular passage through which air is pressurized by the blower and conducted from the blower to a convective device in a convective treatment system. Hereinafter, the term "air hose" will be used in place of "air supply duct" in order to convey the sense of a flexible tubular passage. The air hose has two ends, one for connection to the blower, the other for connection to the convective device. For convenience of this description, and for no other purpose, the end that is to be connected to the convective device may also be called a "distal" end. In the context of the invention, it is presumed that the air hose conducts pressurized air that is warmed; indeed the air may even be called "hot". This is intended to convey the sense that the temperature of the air has the potential to be raised to a level in a range, and that that level or any other level in the range results in a nozzle temperature that poses a risk of harm to a person if blown directly onto the person from the nozzle of the air hose, with the convective device removed.

The term "interface device" is also used in this description. In this application, an interface device is a device, an apparatus, an appliance, or any equivalent structure or means, that wholly or partly closes the distal end of an air hose in order to reduce, restrict, attenuate, or even stop the flow of air out of the air hose. One may also call an interface device a "flow-restricting" member or a "closure", or a "stricture", or any other equivalent term without narrowing or surrendering the full range of equivalents that the term "interface device" is entitled to. As will become apparent the interface device can perform these functions without a nozzle being mounted to the end. Further, the interface device may be received on a nozzle at the end, integrated into the structure of a nozzle at the end, or may itself act also as a nozzle at the end.

The term "inlet port" is used in this description as well. Convective devices employ a variety of inlet port structures. In this application, an inlet port is any component of a convective device configured to allow for the ingress of pressurized air. Inlet ports may come in the form of sleeves, sheets flexible of material, and rigid material with defined openings.

Figure 1A:
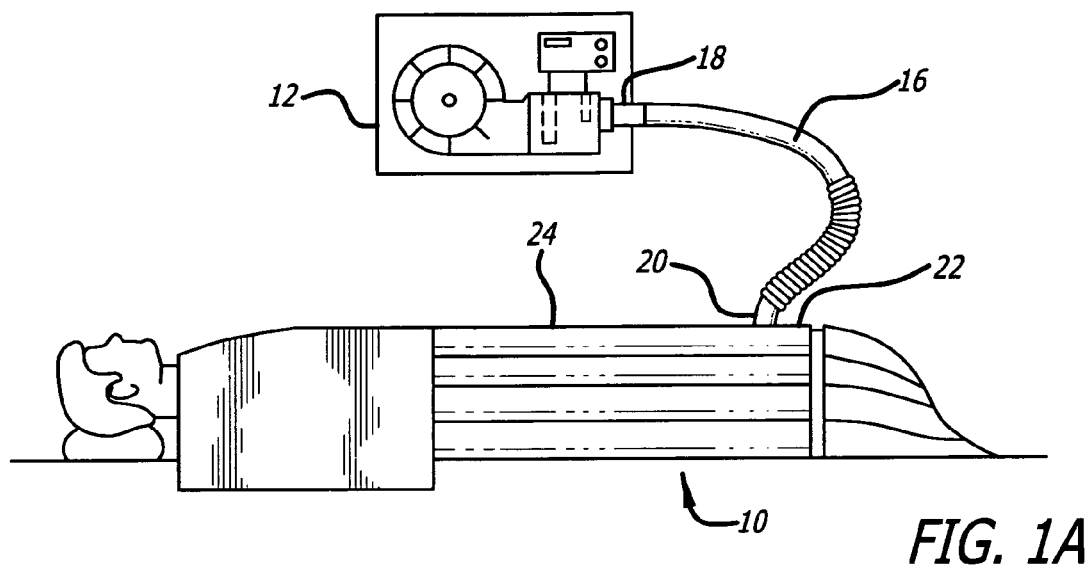
FIGS. 1A and 1B illustrate a convective treatment system in which the invention is deployed.
Figure 1B:
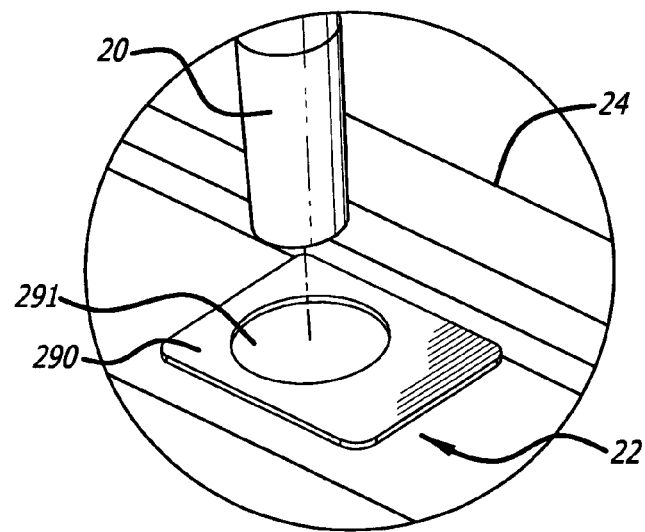

Refer to FIGS. 1A and 1B in which a convective treatment system 10 is illustrated. The elements of the system 10 include a blower 12 that aspirates air from the ambient environment, raises its temperature to a desired level, pressurizes the air above ambient pressure, and discharges the heated, pressurized air at an exhaust port 14. An air hose 16, with two ends, 18 and 20, is provided. The end 18 is connected to the exhaust port 14 and the air hose 16 conducts the heated, pressurized air to the end 20. The end 20 is connected, coupled, or joined to the inlet port 22 of a convective device 24. In this regard, the equivalent action from the point of view of the convective device 24 is that the end 20 is received in, or by, or near the inlet port 22. When the end 20 and the inlet port 22 are thus brought together, the heated, pressurized air is conducted through or out of the end 20 into the convective device 24.

A representative convective device with an inlet port is described in detail in the assignee's U.S. Pat. No. 6,309,408, which is incorporated by this reference. The convective device 24 and its associated inlet port 22 may be understood with reference to the '408 patent, in which an inflatable device has an opening around which is mounted a relatively stiff sheet of cardboard material. The sheet of cardboard material has an opening that is aligned with the opening in the inflatable device. The sheet provides structure to receive, retain and support the end or nozzle of an air hose in an inlet port. This arrangement, shown in FIGS. 15 and 16 of the '408 patent, is instructive in understanding the embodiments which are described below.

Completing the description of the system 10, with reference to the '408 patent as an instructive example, heated, pressurized air is conducted into the convective device 24 which conveys the air from the inlet port 22 into its interior, imposing a heat loss that reduces the temperature level of the air, and extravises the heated, pressurized air through one or more surfaces of the convective device 24. The system 10 thus delivers thermally-regulated air to the convective device 24, and the device distributes the thermally-regulated air around a person or a specific body area of the person.

In order to afford protection from injury that could result should the end 20 become separated from the inlet port 22, either by accident or by intentional action, an interface device that controls the interface between the inlet port 22 and the end 20 is provided. The interface device acts to wholly or partly close the end 20 of the air hose 16 in order to reduce, restrict, attenuate, or even stop the flow of air through the end 20. When the end 20 is connected, coupled, or joined to the inlet port 22, the interface device operates to allow pressurized, thermally-regulated air to flow easily through the end 20 into the convective device 24. Following connection, when the end 20 is disconnected, uncoupled, or separated from the inlet port 22, the interface device operates to wholly or partly close the end 20 in order to reduce, restrict, attenuate, or even stop the flow of air through the end 20. Refer now to the remaining drawings, which illustrate various embodiments of the interface device.

Embodiment of FIGS. 2A-2E.

In FIGS. 2A-2E an interface device that exemplifies this invention is illustrated. The interface device 200 includes two frusto-conical sections 210 and 212 made of any material that can be joined to an end of an air hose and received in and supported by an inlet port such as the inlet port 22. In this regard, taking the air hose 16 as an example, its end 20 may include an annulus 20a made of a material that is easily joined to the material of which the sections 210 and 212 are made. Representative materials for the elements 210, 212, and 20a may include, for example, durable plastics, composites, or any equivalent materials or combinations thereof. The frusto-conical section 210 has a wall 220 through which at least one opening is provided. For example, two opposing openings 221 and 222 are shown in these figures. The opposing openings 221, 222 are elongate, semi-rectangular fenestrations which open through the wall 220. In this example, each of the openings 221, 222 has a major dimension 1 which extends lengthwise on the section 210. A single opening 225, also an elongate semi-rectangular fenestration, opens through the wall 220. This opening 225 has a major dimension 1 which extends crosswise on the section 210. The narrow end 228 of the section 210 has a structural member 229 that extends entirely across it. The member 229 is illustrated as having the shape of an hour glass with rounded ends, although this is not necessary to the practice of the invention. The wide end 230 of the frusto-conical section 210 is open. The frusto conical section 212 acts on or against the frusto-conical section 210 in order to provide relative rotation therewith. In the example shown in these figures, this is accomplished by disposing the section 212 on the inside of the section 210 with its narrow end 248 brought near to or against the inside surface of the narrow end 228 of the section 210 and fixing, joining, or attaching the section 210 to the annulus 20a near the wide end 230 of the section 210. This allows the section 212 to rotate about its axis, at the end 20, within the frusto-conical section 210. In this arrangement, the section 212 has a wall 240 through which at least one opening is provided. For example, two opposing openings 241 and 242 are shown in these figures. The opposing openings 241, 242 are elongate, semi-rectangular fenestrations which open through the wall 240. In this example, each of the openings 241, 242 has a major dimension 1 which extends lengthwise on the section 212. The narrow end 248 of the section 212 has a structural member 249 that extends entirely across it. The member 249 is illustrated as having the same shape as the member 229, although this is not necessary to the practice of the invention. The wide end 250 of the frusto-conical section 212 is open. Each of the sections 210 and 212 is provided with a semi-cylindrical trunnion, with the trunnion 252 being mounted on and projecting outwardly from the wall 220 at the end 229a of the opening 220, and the trunnion 254 being mounted on and projecting outwardly from the wall 240.

Figure 2A:
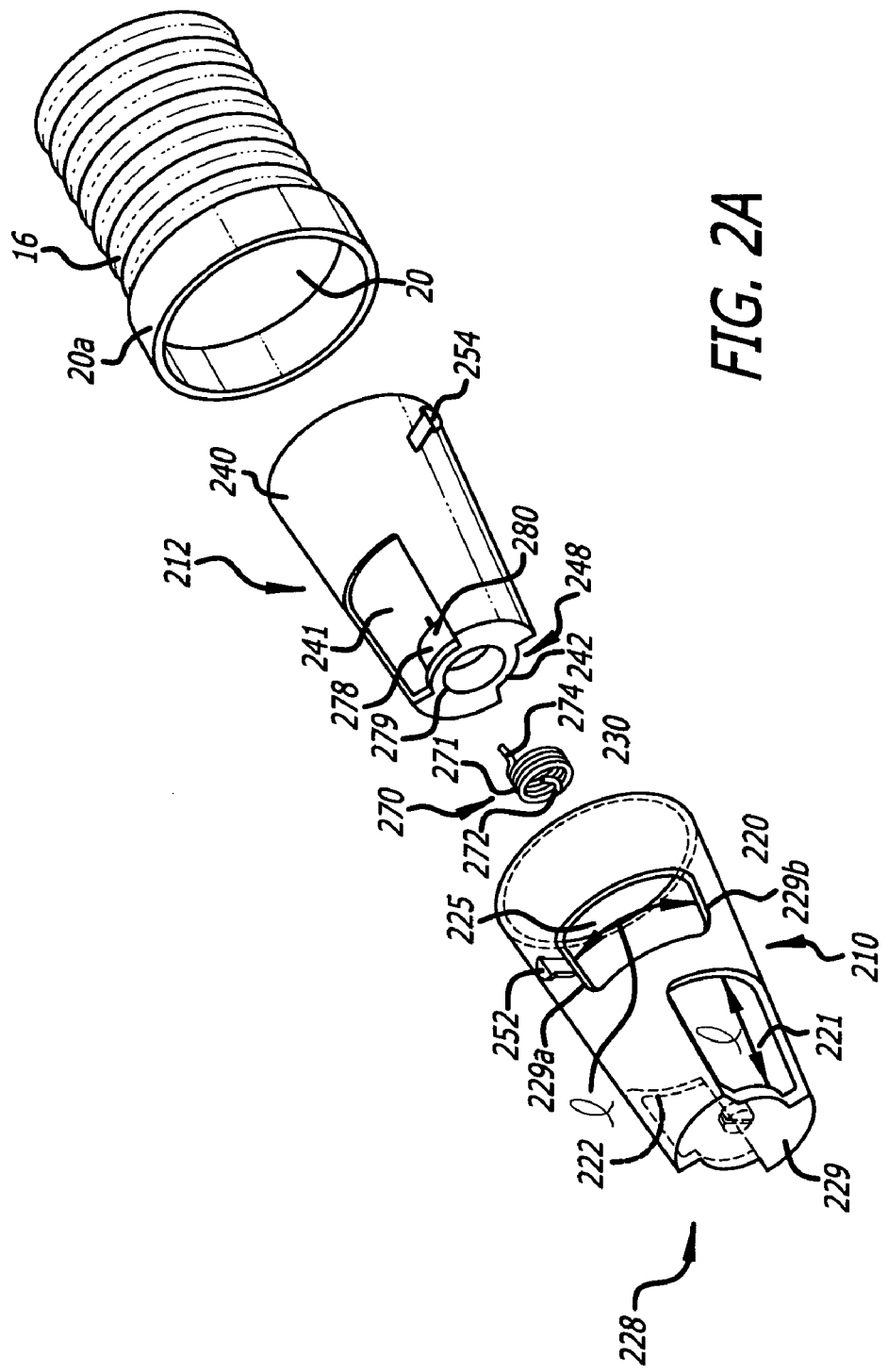
Figure 2C:
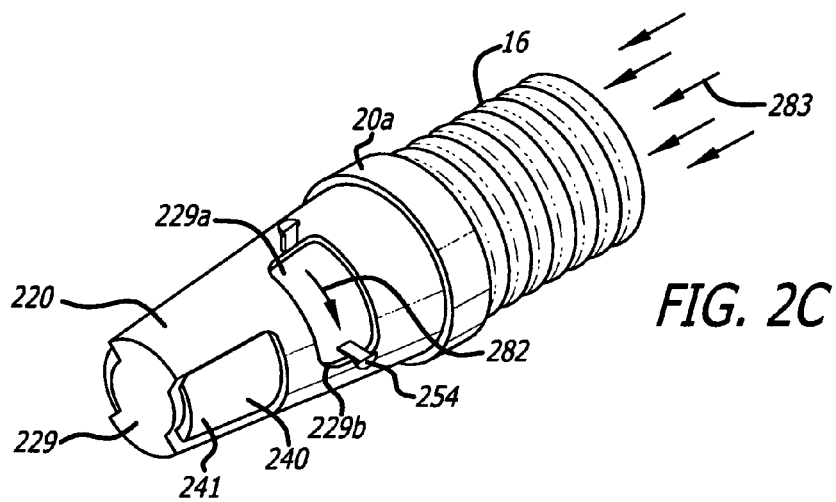
Figure 2D:
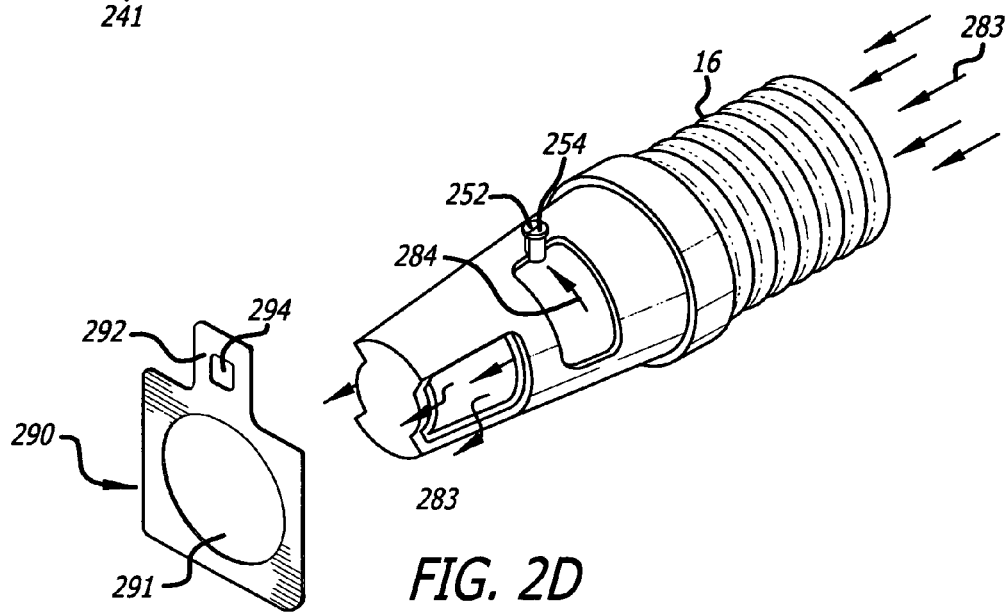

As shown in the figures, especially FIGS. 2A and 2D, the section 212 is received in the section 210, and the wide end 230 of the section 210 is received in and joined to the annulus 20a. The joinder of these elements may be by any appropriate means that substantially or entirely seals the joint between the annulus 20a and the section 210. The joint may be permanent or reducible; it may be immobile or permit rotation between the interface device 200 and the annulus 20a. When the section 212 is received in the section 210, the trunnion 254 extends through the opening 225 in the section 210, constraining the rotation of the section 212 within the section 210 to an arc whose length extends from the end 229a to the end 229b of the opening 225. In these figures, the arc is approximately 90°. When the section 212 is rotated in the direction of arrow 284 toward the end 229a, rotation is stopped at a position of the section 212 where its opposing openings 241, 242 are respectively aligned with the opposing openings 221, 222 of the section 210. At this position, seen best in FIG. 2D, the alignment of the opposing openings provides at least one aperture through the interface device 200 that is in communication with the end 20 and permits air to flow through the air hose 16, to and through the end 20, through the interface device 200, at a relatively high rate. In this figure (and in FIGS. 2C and 2E), air flow is indicated by arrows 283. For example, the rate may be in an operational range from 24 CFM (cubic feet per minute) to 40 CFM. Next, when the section 212 is rotated toward the end 229b, rotation is stopped at a position of the section 212 where its opposing openings 241, 242 are respectively blocked, closed, or shut by the unapertured portion of the wall 220. Similarly, at this position of the section 212, the opposing openings 221, 222 of the section 210 are respectively blocked, closed, or shut by the unapertured portion of the wall 240. At this position, the blocking of the openings 221, 222, 241, and 242, and closure of at least the narrow end 228 of the section 210 reduces, attenuates, restricts or blocks air flowing through the end 20 and the interface device 200. The effect produced thereby can range from wholly cutting off the airflow through the end 20 and the interface device 200 to restricting the airflow therethrough to some rate that is lower than the lower end of the operational range.

As thus far described, the interface device 200 can be operated manually. Self-actuated operation of the interface device 200 can be understood with reference to FIGS. 2A and 2B. In these figures a spring 270 has a coil 271 and two ends 272 and 274. The end 272 is disposed at one end of the spring coil 271, crosswise to the axis of the coil. The end 274 projects from the other end of the spring coil 271 generally parallel to the axis of the coil. A flange 276 projecting into the frusto-conical section 210 from the structural member 229 has a slot 277 that receives the end 272 of the spring 270. A thick annulus 278 is mounted on the rear surface of the structural member 249 of the frusto-conical section 212. A recess 279 is centered in the structural member 249 and the thick annulus 278, and a hole 280 is provided through the member 249 and the annulus 278. The spring 270 is seated in the recess 279 and the end 274 of the spring 270 extends through the hole 280 when the section 212 is received within the section 210. When seated, the spring 270 acts between the frusto-conical sections 210 and 212 by urging the section 212 to rotate in the direction of the arrow 282 until the trunnion 254 engages the end 229b of the opening 225. This stops the frusto-conical section 212 at the position where the flow of air is reduced, attenuated, restricted or blocked. Manual engagement of the trunnion 254 with a force directed in the direction of the arrow 284 moves the trunnion to the end 229a where it abuts the trunnion 252 and rotates the frusto-conical section 212 to the position where the alignment of the opposing openings provides at least one aperture through the interface device 200 that is in communication with the end 20 and permits air to flow from the end 20, through the interface device 200, at the relatively high rate.

Figure 2E:
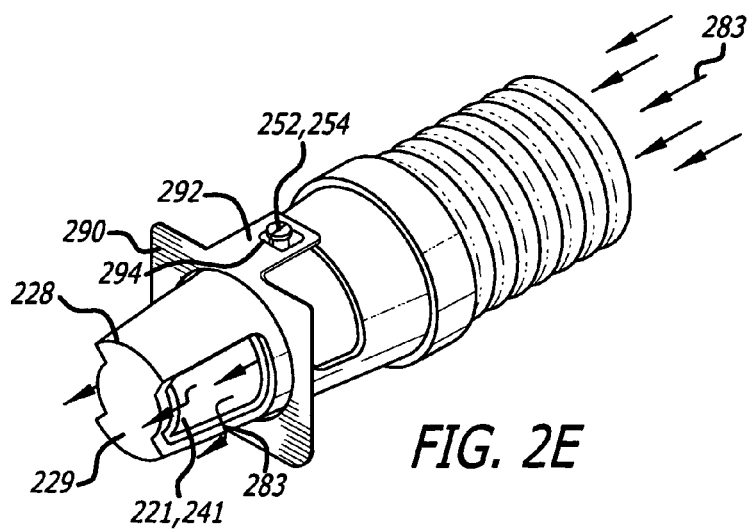

The operation of the interface device with respect to the interface between the end 20 of the air hose 16 and the inlet port can be understood with reference to FIGS. 2C-2E. Assume for illustration that the inlet port 22 includes an inlet port structure such as that disclosed in US Pat. No. 6,309,408, that is to say, the inlet port is in a generally planar sheet of material that is flexible and resilient The inlet port has a shape that permits an air hose nozzle to be engaged with the port, and it would include a sheet 290 of flexible, somewhat deformable material (such as cardboard) In which a port opening 291 is provided. The sheet 290 may also include a tab 292 with an opening 294. The interlace device 200 is mounted to the end 20 of the air hose 16 as described above, and the interface device 200 is mated with the port opening 291, with the narrow ends 228 and 248 oriented toward and extending through the port opening 291. Either before or after the narrow end of the interface device 200 is placed in the port opening 291, the frusto-conical section 212 is rotated in the direction of the arrow 284 until the trunnion 254 is brought against the trunnion 252. This places the section 212 into the position where the alignment of the opposing openings provides at least one aperture through the interface device 200 that is in communication with the end 20 and permits air to flow from the end 20, through the interface device 200, at the relatively high rate. The frusto-conical section 212 can be retained in this position in resistance to the urging of the spring 270 by means of the opening 294 which is brought over the trunnions 252 and 254 by bending the tab 292 toward the interface device 200. Now, if the air hose 16 is disconnected from the inlet port, the tab 292 is bent away from the trunnions 252 and 254, and the spring 270 will urge the frusto-conical section in the direction of the arrow 282 to the position at which the flow of air out of the end 20 is reduced, attenuated, restricted or blocked Embodiment of FIGS. 3A-3E Refer now to FIGS. 3A-3E for an understanding of another embodiment of the interface device. In these figures, the interface device embodiment includes a shutter. In this embodiment, when the end 20 and the inlet port 22 are brought together the shutter opens (or, is opened) to permit pressurized air to flow out of the end 20 into the convective device. Likewise, when the end 20 is separated from the inlet port 22 the shutter closes (or, is closed), to reduce, restrict, or prevent the flow of air out of the end 20, thereby preventing burn accidents or improper operation of the equipment.

The interface device 300 includes an end piece 305 comprising a tubular section 307 and a front piece 309 in the form of a concaved rectangular frame. The front piece 309, disposed on one end of the tubular section 307, has a concaved rectangular surface 311 around the periphery of which a frame with side slots (one indicated by 313) is disposed. A generally triangular opening 315 is disposed generally in the center of the surface 311 and there is a rounded half cylindrical slot 317 disposed on one edge of the opening 315 generally on the longitudinal axis of the surface 311. The end piece 305 is preferably a unitary element formed, possibly, by molding a durable plastic. The end piece 305 is assembled to an annular collar 320 on the end 20, for example by threaded screws that extend through the second end of the tubular section 307, although other joinings are possible. When assembled in this manner, the opening 315 permits pressurized air to flow out of the end 20.

The interface device 300 further includes a flexible shutter 325 having a generally rectangular shape that corresponds to the rectangular shape of the surface 311. The flexibility of the shutter 325 permits it to assume the concaved shape of the surface 311 when the shutter is received in the frame of the front piece 309 with its sides 326 received in the side slots 313. Alternatively, the shutter 325 could be formed of a hard plastic conformed to fit the shape of the surface 311. The shutter 325 is shorter than the surface 311, enabling it to slide thereon. The shutter includes, in one end portion, one or more triangular openings 327. When the shutter is slid away from the opening 315 in the surface 311 to a position against the edge 318 of the end piece, the unbroken portion of its other end portion blocks the opening 315, thereby preventing or restricting the flow of pressurized air out of the end 20. When the shutter 325 is slid toward the opening 315 to a position against the edge 319, the one or more openings 327 align with the opening 315 and permit pressurized air to flow out of the end 20.

The operation of the shutter 325 may be manual or it may be automated by provision of a spring 330. The spring 330 acts between the shutter 325 and the end piece 305, being relatively more compressed when the shutter 325 is slid toward the edge 319, and urging the shutter from that position toward the edge 318. The spring 330 is retained to act in this manner by a gudgeon 328 that projects off one side of the shutter 325 into one end of the spring, in the direction of the cylindrical slot 317, which receives the other end of the spring 330. A retainer 331 extends away from the other side of the shutter 325 and broadens into a tab 333. The shutter 325 is retained against the surface 311, in the frame of the front piece 309 by a concaved rectangular cover 340 having a center opening 341 aligned with the opening 315. An elongate slot 343 opens into the periphery of the center opening 341, and an arcuate lip 342 is provided adjacent the periphery of the center opening 291, diametrically opposite the slot 343. The retainer 331 projects through the slot 343 and traverses the slot from end to end as the shutter 325 is moved between the positions described above. When the shutter 325 is slid to the position at which it is stopped against the edge 319, the openings 315, 327, and 341 align, permitting pressurized air to flow out of the end 20. At this position, the retainer 331 is retained against the arcuate lip 345.

Figure 3A:
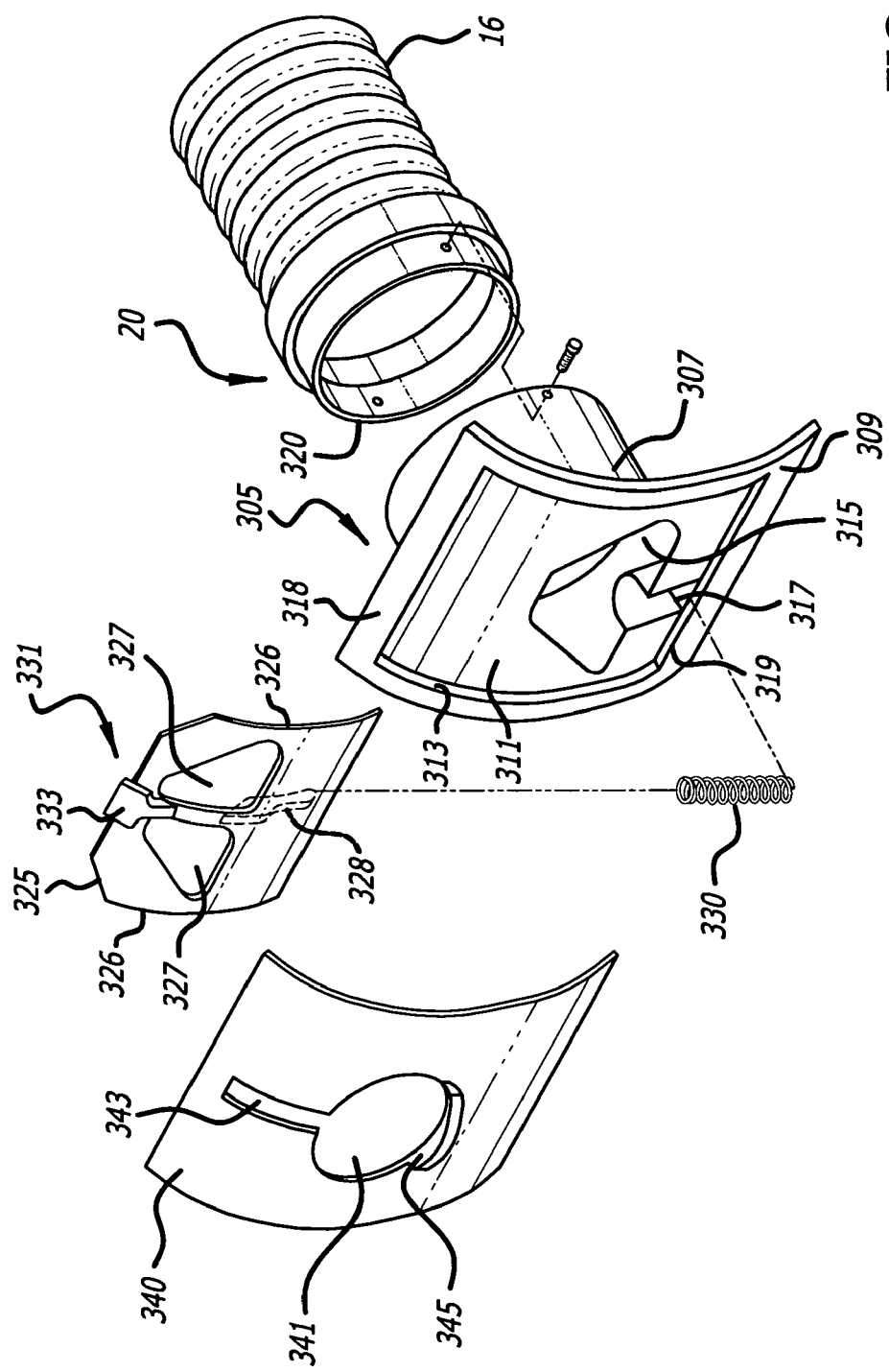
FIGS. 3A-3E illustrate another embodiment of an interface device according to the invention.
Figure 3B:
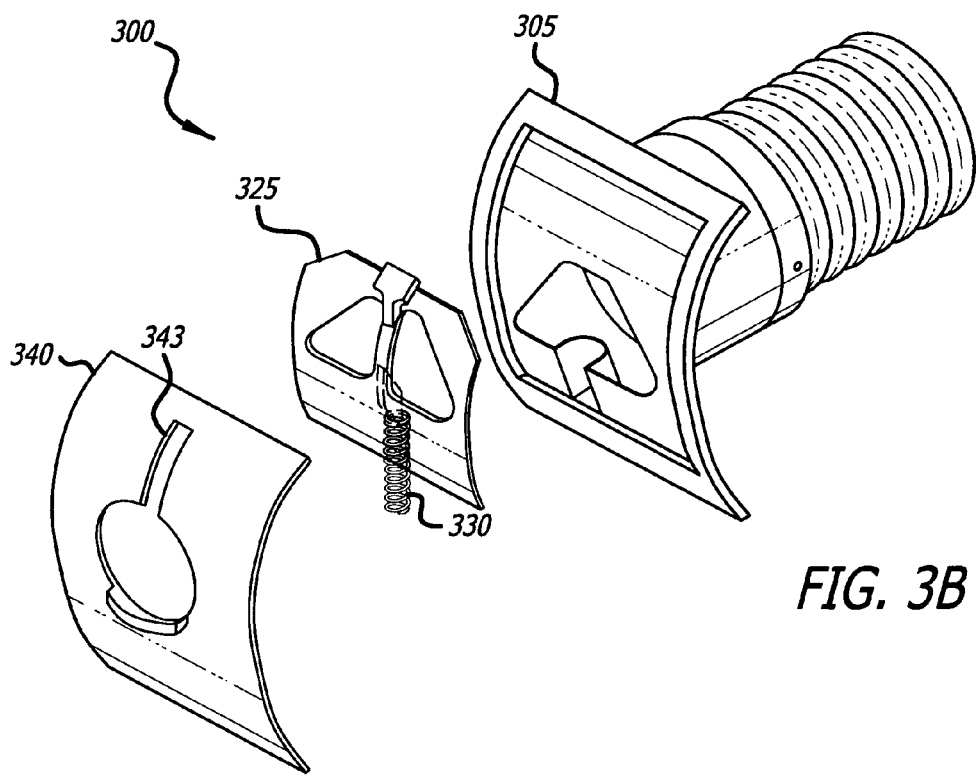
Figure 3C:
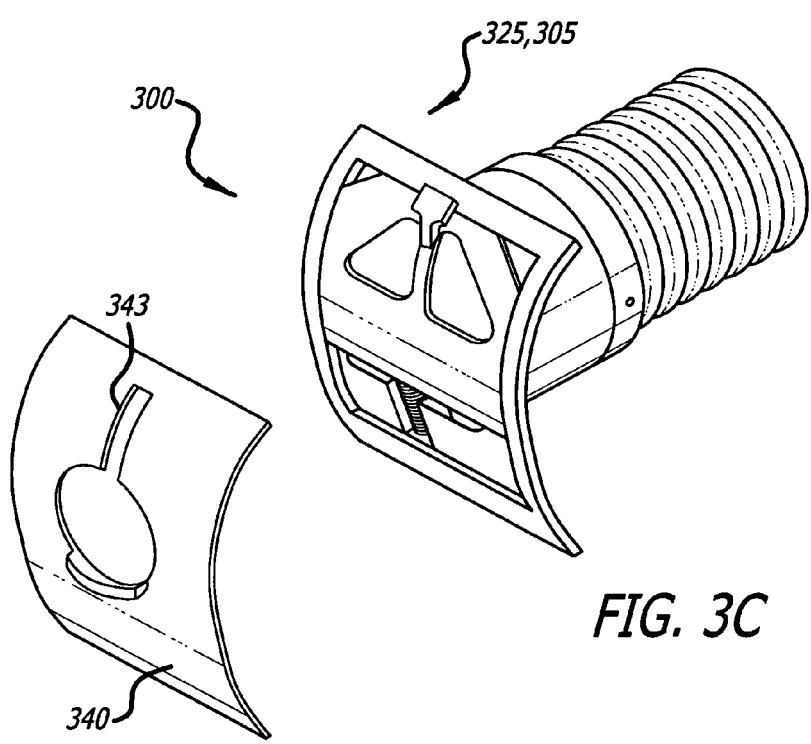
Figure 3D:
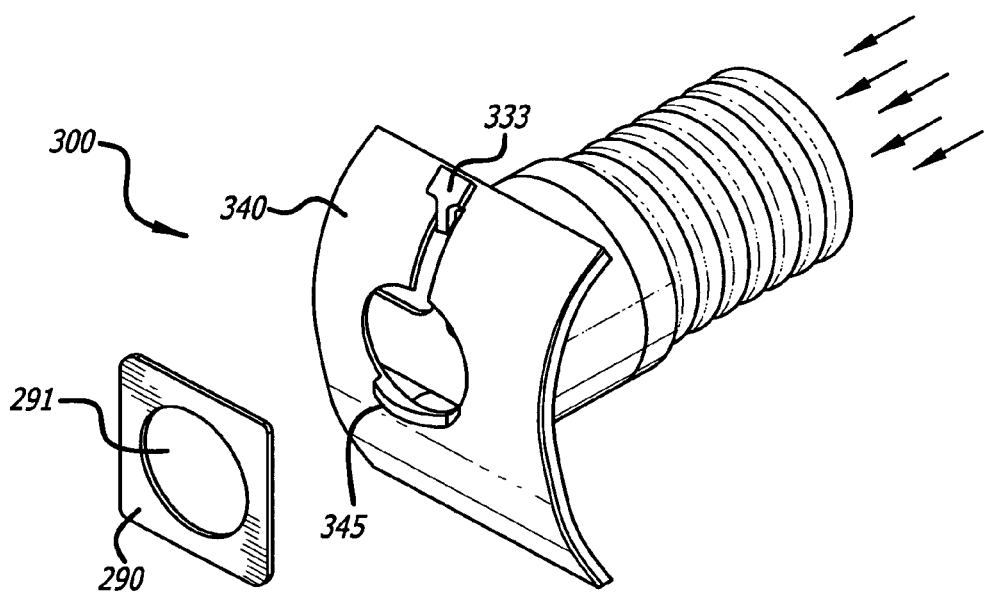
Figure 3E:
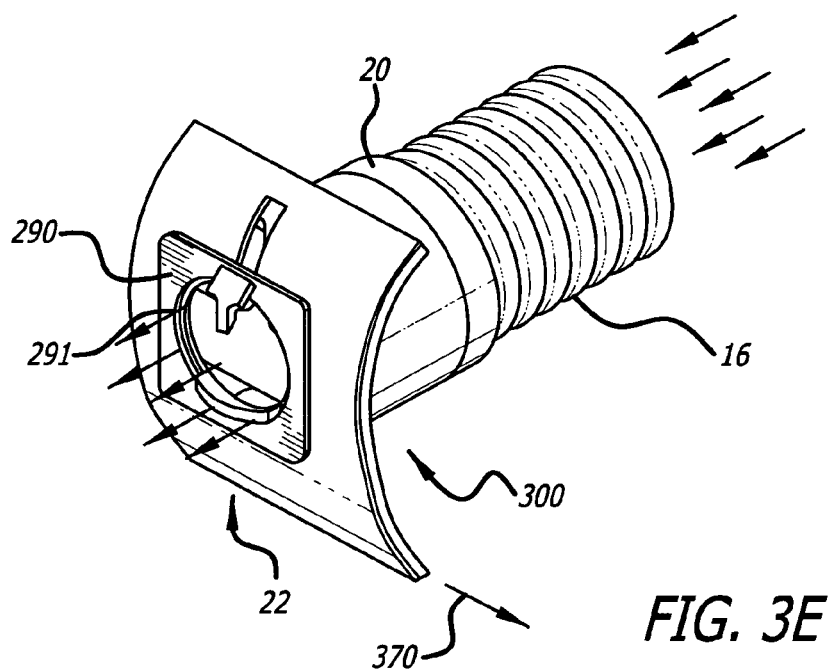

A self-actuating operation of the interface device 300 is best seen in FIGS. 3D and 3E. To bring the end 20 together with the inlet port 22, the shutter 325 is slid toward the edge 319 by pressure applied against the tab 333. With the shutter 325 held in this position, the end piece 305 is brought against the sheet 290 of the inlet port 22, with the tab 333 extending through the port opening 291. The compressed spring 330 urges the retainer 331 into engagement against the periphery of the port opening 291. This keeps the shutter in the position at which pressurized air flows out of the end 20, through the inlet port 22. The end 20 is separated from the inlet port 22 by sliding the end piece against the sheet 290 in the direction of the arrow 370. This disengages the tab 333 and allows the shutter to be returned by the spring 330 to the position against the 318 where the opening 309 is blocked, covered, or closed by the unaperatured portion of the shutter 325.

Embodiment of FIGS. 4A and 4B

Refer now to FIGS. 4A and 4B for an understanding of another embodiment of the interface device. In these figures, the interface device embodiment 400 includes a sleeve 418 of flexible material having an open end 422 that transitions to a shallow bowl-like collar and an end 424 that has a normally closed configuration in which opposing sections of the sleeve 418 at the end 424 abut without being permanently joined. The sleeve 418 is made of a durable flexible plastic such as polypropylene or polyethylene and has a remembered shape that maintains the end 424 in its normally closed configuration. Opposing longitudinal living hinges 415 and 417 connect two opposing segments 419 and 420 of the sleeve 418. Forces applied in opposition to the living hinges 415 and 417 near the end 424 (indicated by arrows 435) cause the end 424 to open and the sleeve 418 to assume an open tubular configuration. When the opposing forces 435 are released, the sleeve 418 returns to its remembered shape in which the end 424 is in its normally closed configuration.

The interface device 400 is operated by applying opposing forces to each side of the sleeve 418, on the living hinges 415 and 417, near the end 424 as indicated by the arrows 435 in FIG. 4B. This opens the end 424 into a roughly cylindrical shape that is received in the port opening 291. The end 424 is inserted into the port opening 291, and the opposing forces are released. This causes the sleeve to seek its remembered shape, and engage the rim of the port opening 291, thereby retaining the now-open end 424 within the port opening 291, permitting air to flow from the end 20, through the interface device 400, at the relatively high rate. To withdraw the interface device 400 from an inlet port, opposing forces are again applied to the sleeve 418 to flex the sides of the sleeve 418 at the living hinges 415, 417 in the directions indicated by the arrows 435, thereby disengaging the sleeve 418 from the port opening 291 and allowing the end 424 to be withdrawn from the port opening 291. When the end 424 is withdrawn from the inlet port and the opposing forces 435 are released, the sleeve 418 returns to its remembered shape, thereby returning the end 424 to its normally-closed configuration, in which the flow of air out of the end 20 is reduced, attenuated, restricted or blocked.

Figure 5A:
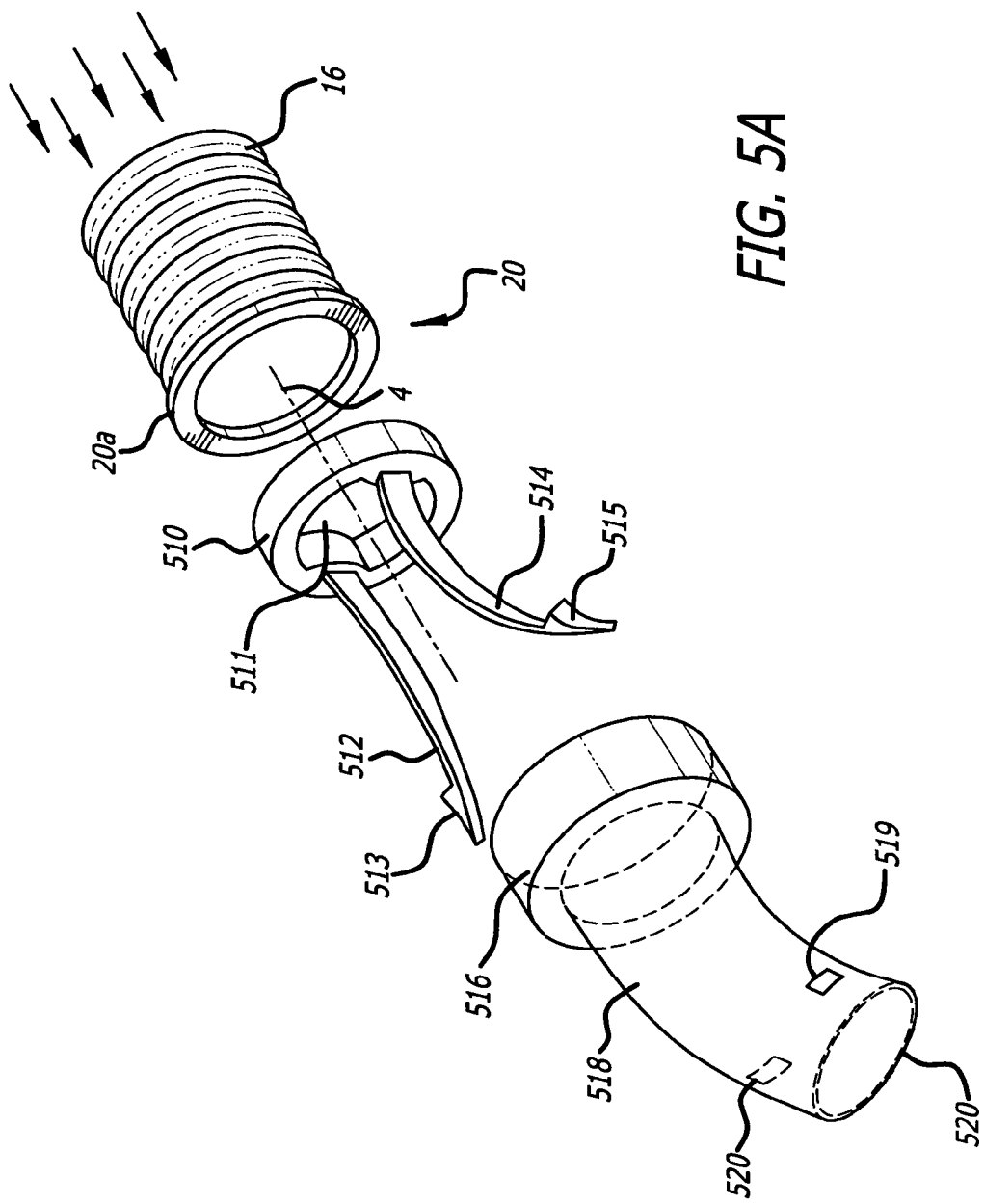
FIGS. 5A-5C illustrate another embodiment of an interface device according to the invention.
Figure 5B:
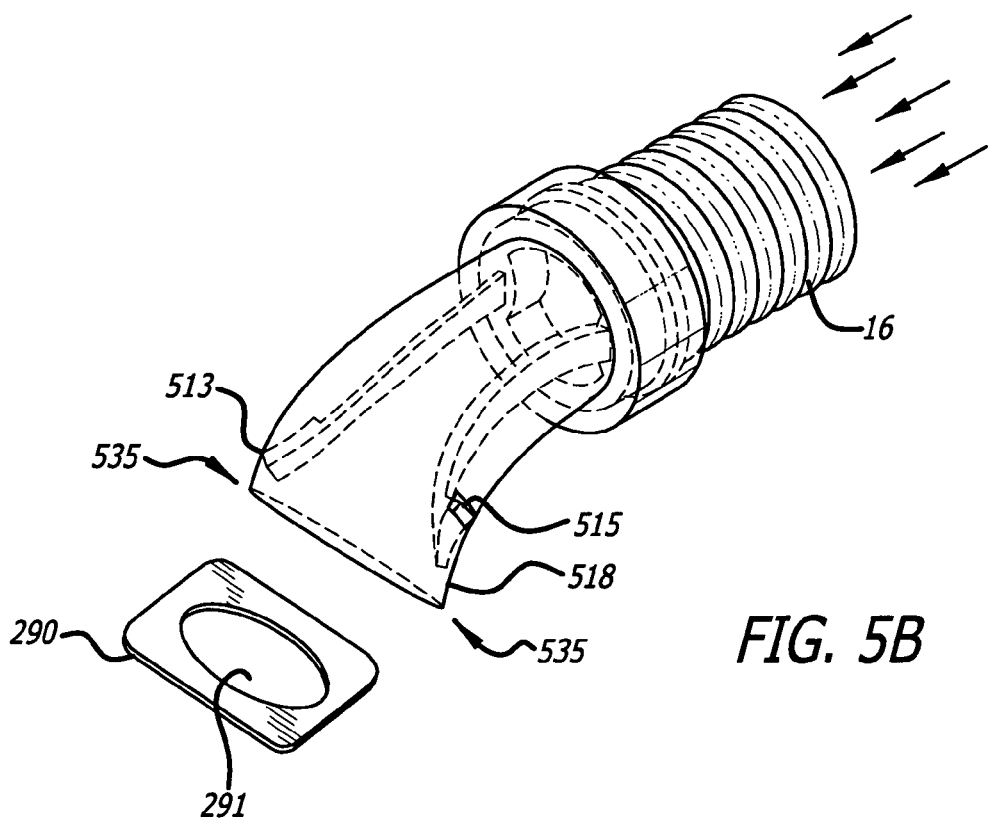
Figure 5C:
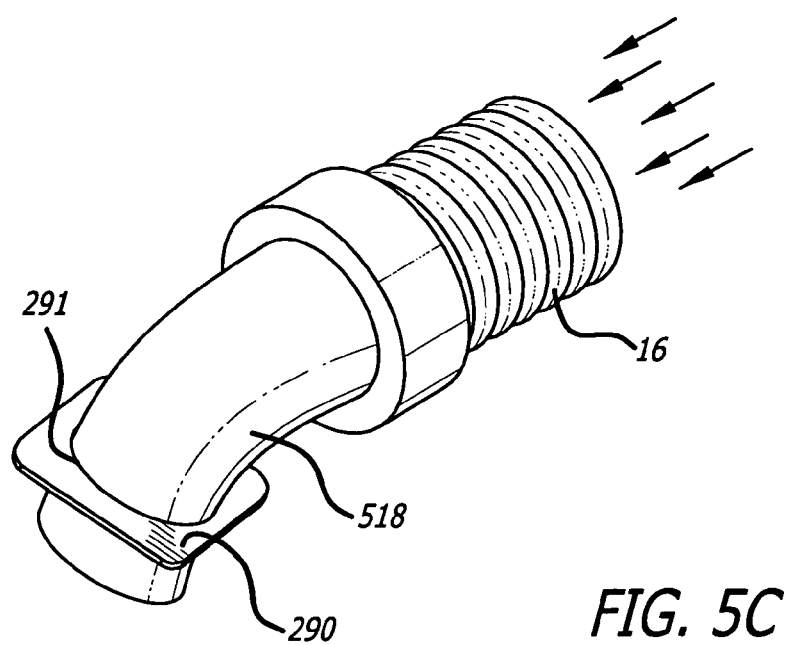

Embodiment of FIGS. 5A-5C

Refer now to FIGS. 5A-5C for an understanding of another embodiment of the interface device. In these figures, the interface device embodiment 500 includes a spring structure with a base ring 510 having an opening 511. An imaginary axis A, centered in and perpendicular to the base ring 510, may be defined. A pair of elongate flexible tines 512 and 514 are mounted in opposition on one surface of the base ring 510, extending along and beside the axis A. The other surface of the base ring 510 has the same shape and dimensions as the annulus 20a. The flexible tines 512 have the shapes of shallow descending arcs that open in opposite directions away from the axis A. The flexible tines 512 and 514 are formed from any appropriate flexible material that retains a memory of its original shape when flexed by an applied force and that returns to the remembered shape when the force is removed. One such material is a sturdy, durable plastic such as polypropylene or polyethylene. The flexible tines 512 and 514 have wedge-shaped tips with vertices 513 and 515, respectively, that extend outwardly from the tines. A sleeve 518 of durable flexible material such as polypropylene or polyethylene is molded into a shape having opposing ends 522 and 524, wherein the end 522 transitions to a shallow bowl-like collar and the end 524 has a normally closed configuration in which opposing sections of the sleeve at the end 524 abut without being permanently joined. Force applied in opposition to the sides of the end 524 cause the end 524 to open. Opposing apertures 519 and 520 are provided through the sleeve 518 near the end 524. The interface device 500 is assembled by attaching, joining, or bonding the base ring 510 concentrically to the annulus 20a and then sliding the sleeve 518, end 522 first, over the tines 512 and 514, until the end 522 is brought against the base ring 510. When the end 522 is seated against the base ring 510, the vertices 513 and 515 are received in and protrude through the apertures 520 and 519. The end 522 is attached, joined, or bonded to the base ring 510. When assembled, the interface device is maintained in a normally closed configuration by the tines 512 and 514 which seek their remembered shapes, exerting drooping outwardly-directed opposing forces on the end 524, which maintains the end 524 in its normally-closed configuration. As best seen in FIGS. 5B and 5C, the drooping component of the curvature of tines 512 and 514 imposes a pronounced hook on the portion of the sleeve 518 that includes the end 524. The interface device 500 is operated by applying opposing forces to each side of the sleeve 518, near the end 524 just behind the vertices 513 and 515, as indicated by the arrows 535 in FIG. 5B. This opens the end 524 into a roughly cylindrical shape that is received in the port opening 291. The end 524 is inserted far enough into the port opening 291 to place the vertices 513 and 514 through the port opening 291 where they engage the back surface of the sheet 290. When the opposing forces are removed, the tines 512 and 514 seek their remembered shapes and retain the now-open end 524 within the port opening 291, permitting air to flow from the end 20, through the interface device 500, at the relatively high rate. To withdraw the interface device 500 from an inlet port, opposing forces are again applied to the sleeve 518 to flex the sides of the sleeve 518 and the tines 512 and 514 in the directions indicated by the arrows 535, thereby disengaging the vertices 513 and 514 from the sheet 290. When the end 524 is withdrawn from the inlet port and the opposing forces 535 are released, the tines 512 and 514 seek their remembered shapes, thereby returning the end 524 to its normally-closed configuration, in which the flow of air out of the end 20 is reduced, attenuated, restricted or blocked.

Embodiment of FIGS. 6A and 6B

Refer now to FIGS. 6A and 6B for an understanding of another embodiment of the interface device. In these figures, the interface device embodiment 600 includes a single frusto-conical section 610 made of a durable flexible material such as plastic and having a narrow end 628 and a wide end 630. Both of the ends 628 and 630 are open, and the wide end 630 transitions to a shallow bowl-like collar. At the narrow end 628 there are four elongate slots 612 that extend from the end 628 longitudinally along the section 610 for about a third of the length of the section 610. The slots are arrayed at 90° around the narrow end 628 of the section 610 and define four corresponding legs 614 extending from the narrow end 628. The legs 614 are flexible and can be flexed inwardly toward one another. A ball or sphere 620 of light durable material such as plastic is disposed on the inside of the section 610, wherein it is free to move between the narrow end 628 and the wide end 630. The ball 620 has a diameter that fills the narrow end 628. The ball 620 may be hollow and have apertures therein to allow a limited amount of air to pass through the ball itself. Although not shown in these drawings, the ball 620 may be tethered to the inside of the section 610, or constrained therein by a cross piece at the wide end 630. The interface device 600 is assembled by receiving the annulus 20a in the shallow bowl-like collar at the wide end 630 where it is attached, joined, or bonded to the collar.

The interface device 600 is operated by squeezing together the legs 614. The narrow end 628 is inserted into the port opening 291, which, for this embodiment may have a quatrefoil pattern for receiving the legs 614. When the squeezing force is removed from the legs, they spring back toward their unflexed positions and frictionally engage the port opening 291. Alternatively, the engagement of the port opening 291 may be effected by relying on the taper of the legs 614. In this case as the interface device 600 engages sheet 290, the wide end of the tapered leg 614 results in a friction fit with the opening 291 The quatrefoil pattern of the port opening prevents ball 620 from entering the narrow end 628, permitting air to flow from the end 20, through the interface device 600, at the relatively high rate. To withdraw the interface device 600 from an inlet port, the legs 614 are again squeezed together until they are disengaged from the port opening 291. When the narrow end 628 is withdrawn from the inlet port and the squeezing force is released, the legs 614 seek their remembered positions, and the ball 620 is now free to enter the narrow end 620, where it is impelled by the pressurized air flowing through the end 20. Here, the ball 620 in reduces, attenuates, restricts or blocks the flow of air out of the end 20.

Figure 7A:
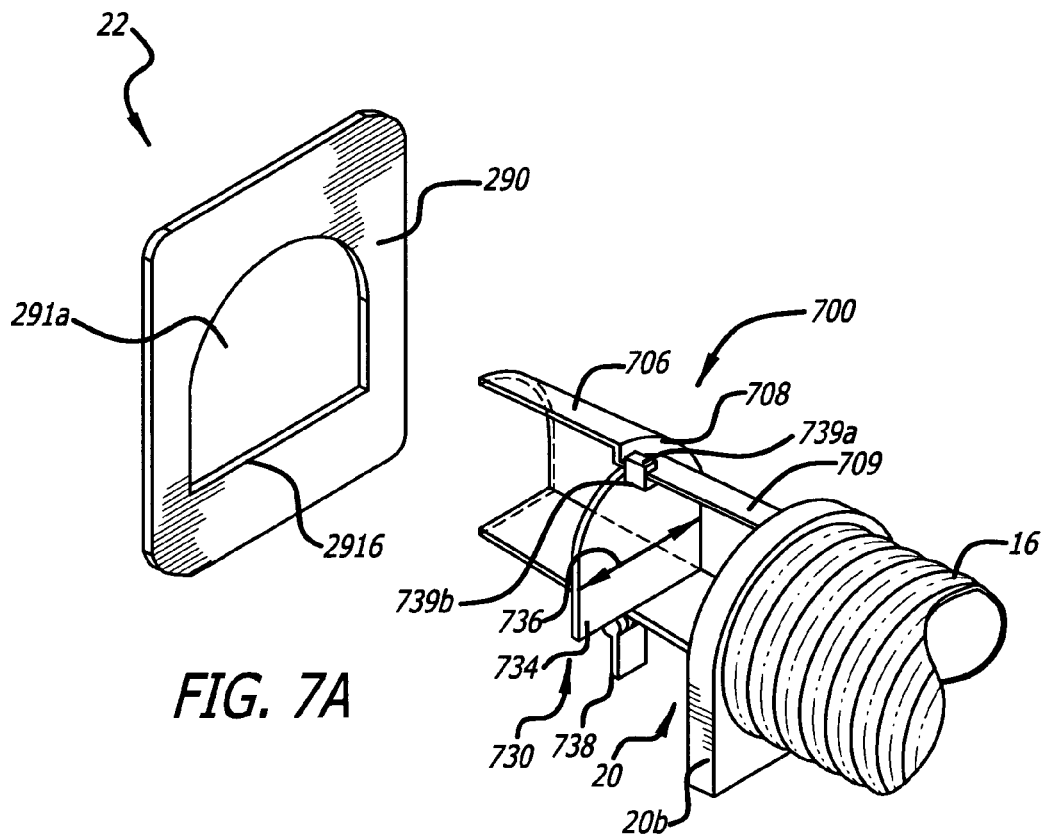
FIGS. 7A and 7B illustrate another embodiment of an interface device according to the invention.

Embodiments of FIGS. 7A/7B 8A-8B, and 9A/9B

FIGS. 7A, 7B, 8A-8C, 9A and 9B contain subject matter originally disclosed in FIGS. 14A, 14B, 15A-15C, 16A, and 16B, respectively, of U.S. patent application Ser. No. 09/546,078 from which this application is continued, in part. In these figures another embodiment of the interface device relies on the opening and closing of a valve to control the flow of air out of the end 20. In this embodiment, bringing the end 20 and the inlet port 22 together causes the valve to open and permits pressurized air to flow out of the end 20 into the convective device. Likewise, separating the end 20 from the inlet port 22 causes the valve to close, reducing, restricting, or preventing the flow of air out of the end 20, thereby preventing burn accidents or improper operation of the equipment.

Figure 7B:
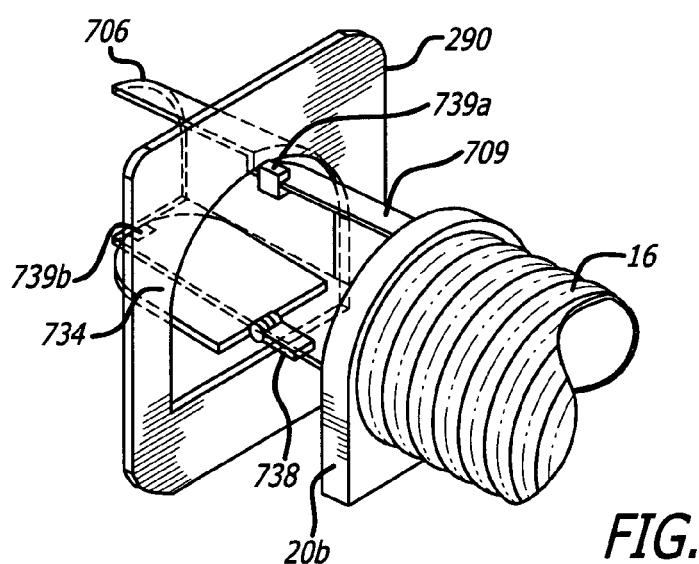

FIG. 7A depicts an inlet port 22, the end 20, and a nozzle 700 (shown partially received in the end 20 for illustration only). The nozzle 700, received in the end 20 of the air hose 16, includes a valve 730. As seen in FIG. 7B, as the nozzle 700 is received in the inlet port 22, the valve 730 including a flap 734 cooperates with the inlet port 22 to enable airflow out of the end 20 through the inlet port 22. Also, while FIG. 7B depicts the valve flap 734 opening toward the inlet port 22 upon activation, it is also possible to design a valve system in which the flap 734 opens towards the air hose 16 upon activation.

The nozzle 700, preferably made of a durable material such as a hard plastic or equivalent, has an arch-shaped forward section 706, that transitions to a shoulder 708. The shoulder 708 transitions to a rear arched-shaped section 709. The rear section 709 is enabled to fit snugly to the end 20 of the air hose 16, by means of an adapter 20*b*. The nozzle 700 is assembled, attached, or brought together with the air hose 16 by inserting the nozzle 700, rear section 709 first, into the adapter 20*b* so far as to bring the shoulder 708 against the adapter 20*b*. There, the shoulder 708 may be bonded to one side of the adapter 20*b*, the other side of which is bonded to the end 20 of the air hose 16.

The end 20 and the inlet port 22 are brought together by inserting the arched-shaped section 706 into the port opening 291*a* (which has an arched shape that corresponds to that of the section 706) open end first, and sliding the section 706 into the opening 291 until the engagement between the valve 730 and the opening 291 cause the valve to open, as is explained below.

The flap 734 has an arched shape with a dimension 736 substantially the same as the corresponding inner dimension of the arch-shaped section 709. It should be noted that the flap 734 need not perfectly seal the end 20 to be effective. The flap 734 stops, blocks, or restricts the flow of air, or substantially stops, blocks or restricts the flow of air, when the end 20 is not received in the inlet port 22.

As depicted in FIGS. 7A and 7B, in addition to the flap 734, the valve 730 includes a hinge lever 738 which is rigidly attached to the flap 734. At the intersection of the hinge lever 738 and flap 734 is an axle or pin (not shown) about which the flap 734 and hinge lever 738 pivot. The hinge lever 738 cooperates with the inlet port 22, being moved from a position perpendicular to the air hose 16, to a position against the air hose 16, to permit the end 20 to be brought together with the inlet port 22. The engagement of the hinge lever 738 with the lower edge 291*b* of the opening 291*a* rotates the flap 734 from a position blocking the flow of air (shown in FIG. 7A) to a position (open position) in which air may flow when the end 20 is brought together with the inlet port 22. Not specifically shown is the mechanism which returns the flap 734 from the open position to the blocking position (FIG. 7A) when the end 20 is disengaged from the inlet port 22. The return- mechanism can be a spring or some such torsioning member (not shown) which is put under load by the action of the flap 734 being forced into the open position (FIG. 7B). Additionally, in some orientations, the flap 734 can be returned to its seated position by the frictional force of the airflow within the air hose 16. Once the valve flap 734 is seated, it will be held in place by the static pressure developed by the blower.

Optionally, a pair of magnets 739*a* and 739*b* may be used to keep the flap 734 in the blocking position when the end 20 is separated from the inlet port 22. The first magnet 739*a*, is disposed in the rear section 709 and the second magnet 739*b* is disposed the flap 734. The first magnet 739*a* cooperates with the second magnet 739*b* so that the flap 734 blocks the flow of air when the end 20 is separated from the inlet port 22. Although not specifically shown, magnets can also be used with the flap 734 of the actuator mechanisms shown in FIG. 8A, described below. In another aspect of this embodiment, not shown, the flap 734 may be opened in the direction of the air hose 16 instead of the inlet port 22, so that the flow of air through hose 16 acts to close the flap 734 when it is not engaged.

Figure 8A:
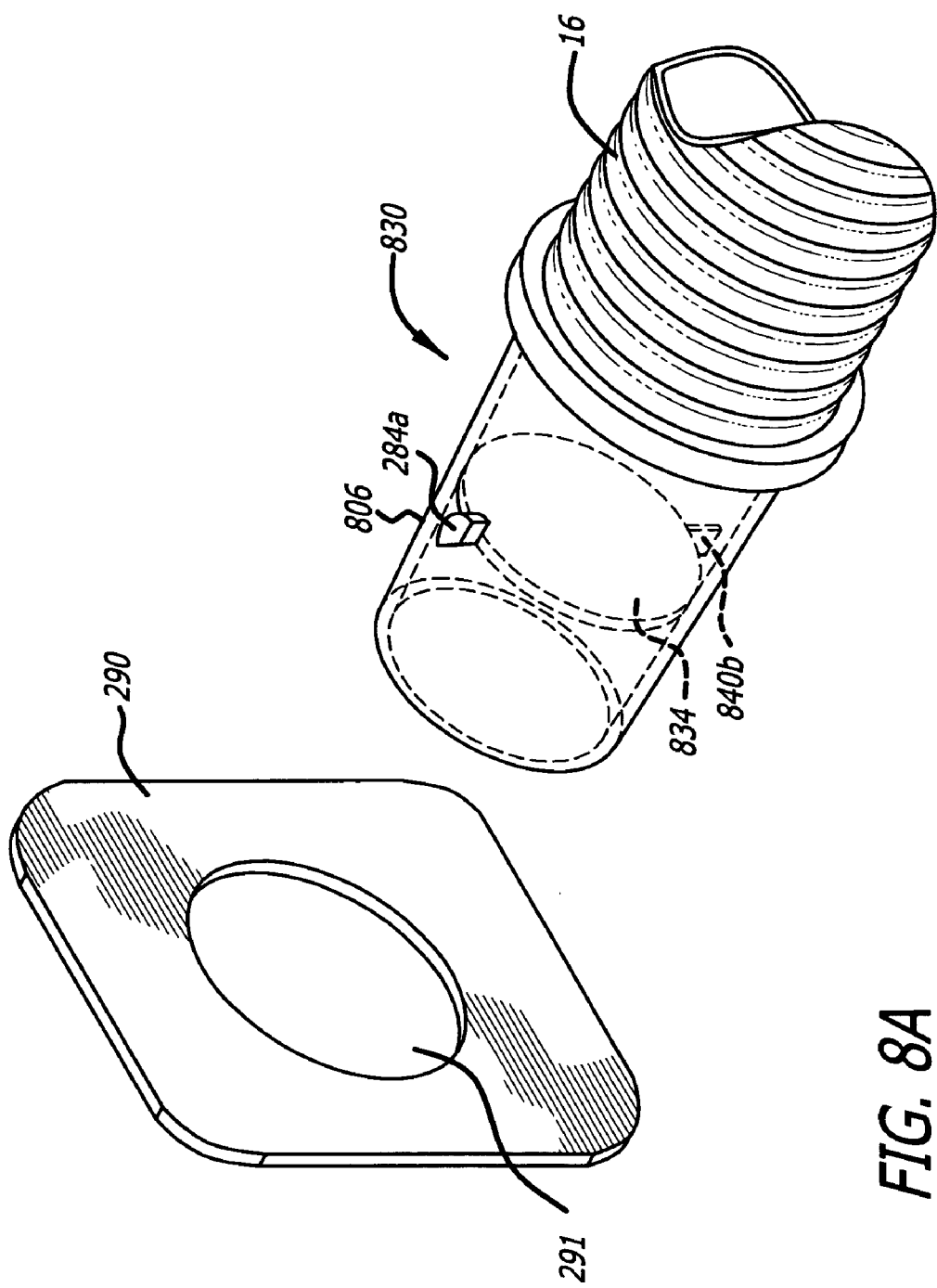
FIGS. 8A-8C illustrate another construction of the embodiment of FIGS. 7A and 7B.
Figure 8B:
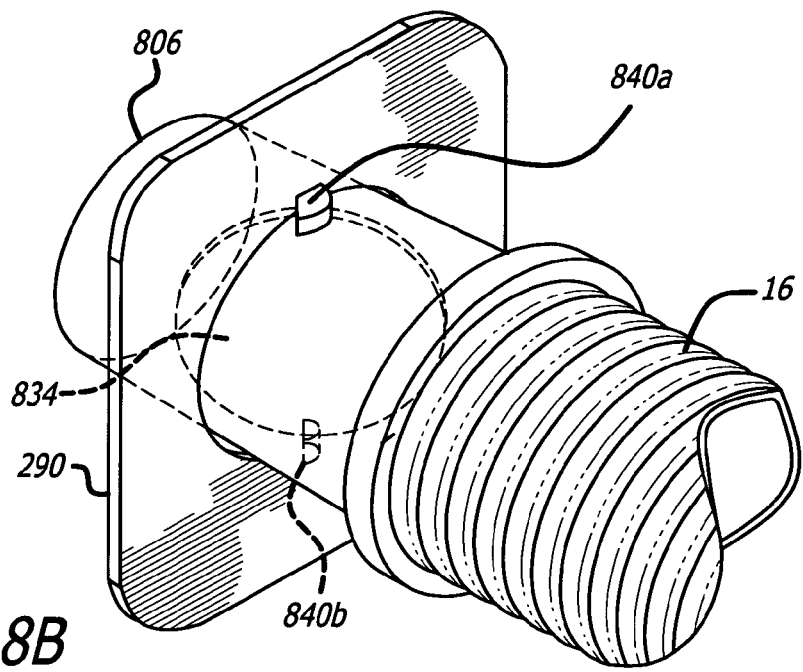
Figure 8C:
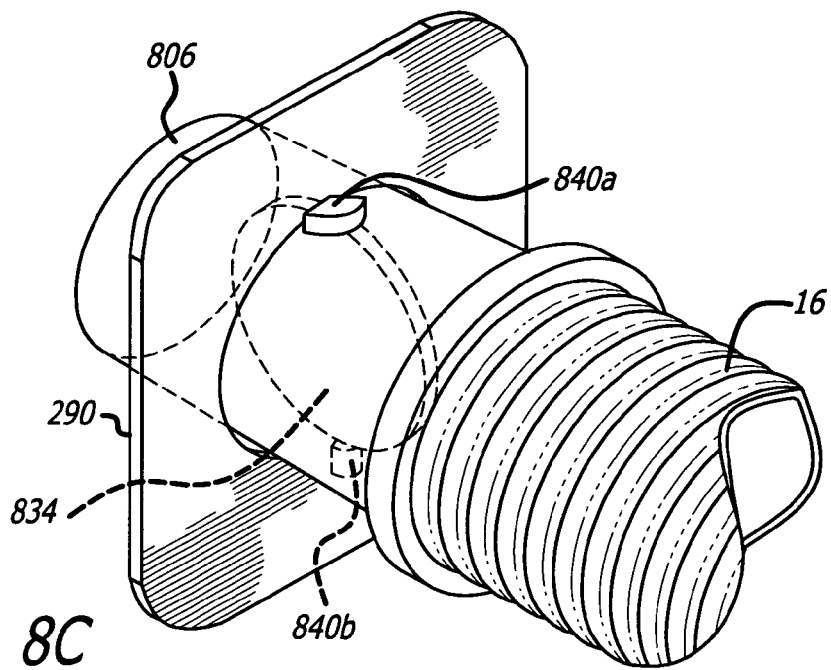

FIGS. 8A through 8C depict a valve 830 with a circular valve flap 834, coupled to a cam actuation mechanism, and disposed in a single, substantially tubular section 806. The tubular section 806 is attached, at one end to the end 20 of the air hose 16. The flap 834 has a diameter substantially equal to the diameter of the tubular section 806. As shown in FIG. 8A, the flap 834 includes a pair of cams 840*a* and 840*b* rigidly attached to the flap 834, 180 degrees apart. Alternately, the cam can be attached to an axle running through the diameter of the flap 834, with the axle being rigidly attached to the flap, so that the face of the flap and the cam facets remain in a fixed relationship. The cam actuation mechanism includes rounded surfaces which permit the cams 840*a*/840*b*, and attached flap 834, to rotate as the cam engages the surface surrounding the inlet port 22. The rotation of the cams 840*a*/840*b* is shown if FIG. 8B. As shown in FIG. 8C, the flat facet surfaces of the cams 840*a*/840*b* permit those surfaces to fixedly seat against the inlet port 22 as the end 20 and the inlet port 22 are brought together. With the cams 840*a*/840*b* seated, the flap 834 is locked in an open position to permit the flow of air. Not shown is a return mechanism which forces the flap 834 into the blocking position (FIG. 8A). As above, the return mechanism can be a spring, or equivalent that is put under load as the flap 834 is forced into the open (non-blocking) position.

Figure 9A:
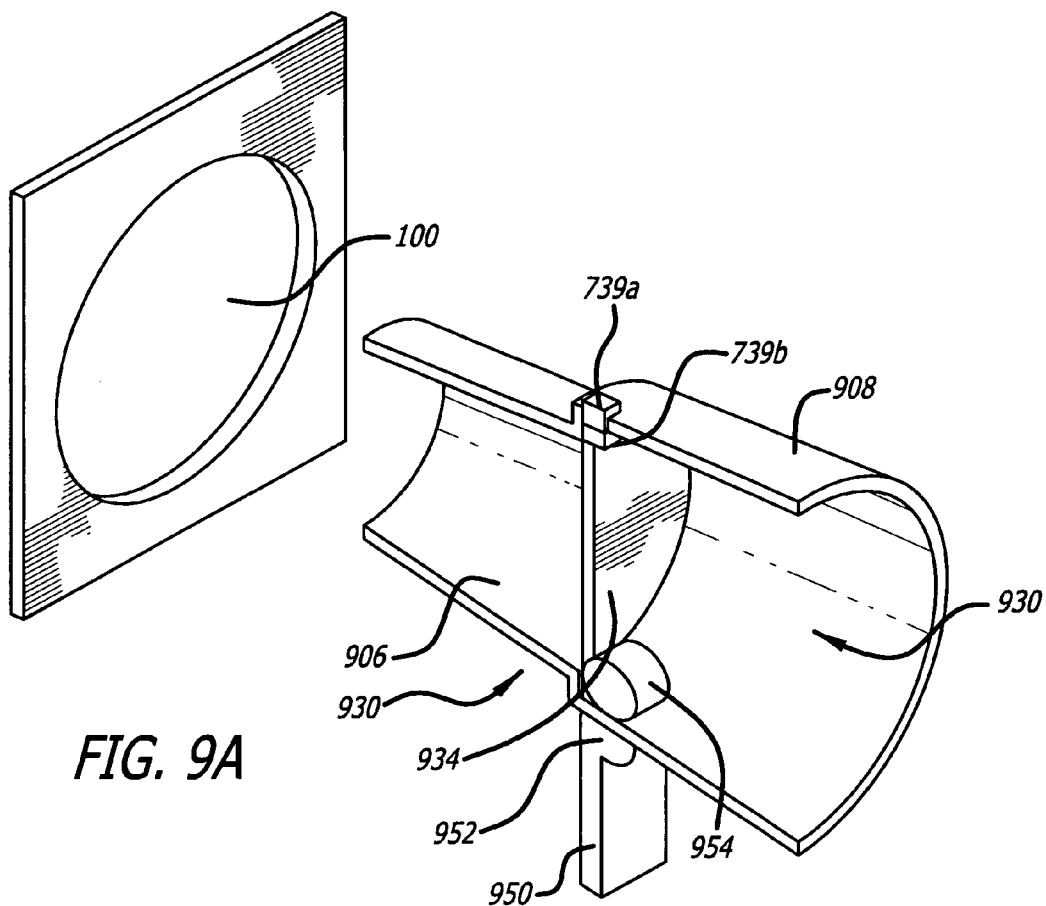
FIGS. 9A and 9B illustrate another construction of the embodiment of FIGS. 7A and 7B.
Figure 9B:
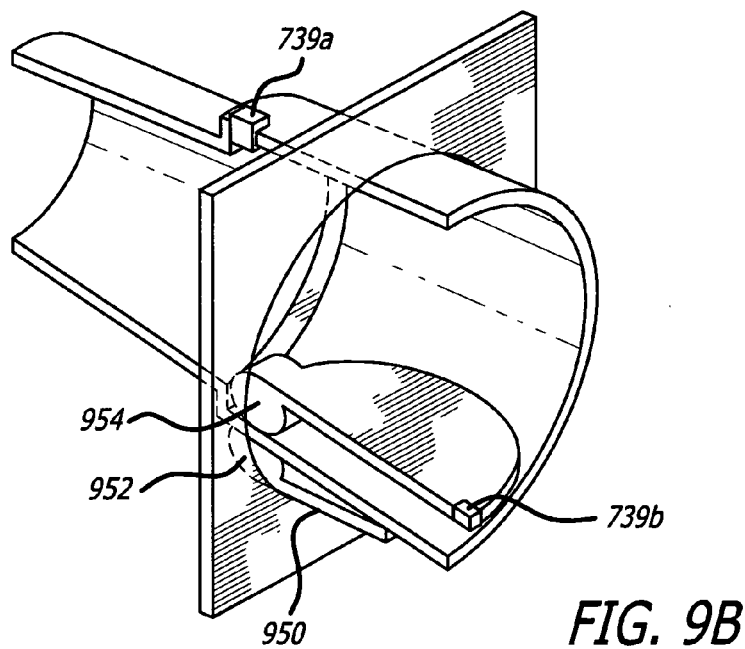

FIGS. 9A and 9B depict a gear rack valve actuator mechanism for a valve 930 having a circular valve flap 934. The mechanism includes a lever 950 which engages the inlet port 22 to open the flap 934. The lever 950 is connected to a first gear 952, the teeth of which are intermeshed with the teeth of a second gear 954. In turn, the second gear 954 is attached to the flap 934. As the lever 950 is engaged, it is forced into the body of the hose 16. The action of the lever 950 and the gears 952/954 open the flap 934 so that pressurized air can pass out of the end 20 into inlet port 22. Optionally the a pair of magnets 739a/739b are used to keep the flap 934 in the blocking position when the end 20 is separated from the inlet port 22. Alternatively, the opening of the flap 934 into the direction of the airflow acts to force the flap 934 into a blocking position when lever 950 is not engaged by the inlet port 22.

We claim:

1. A combination for controlling airflow out of an air hose, comprising:
    an inlet port including a generally planar sheet of flexible material with a port opening for receiving pressurized air from an end of an air hose; and,
    an interface device to act between the end and the inlet port by opening the end when the end is received by the inlet port and to close the end when the end is separated from the inlet port, in which the interface device includes:
        a first frusto-conical section received on the end, the first frusto-conical section including a surface with at least one airflow aperture; and,
        a second frusto-conical section received on the first frusto-conical section the second frusto-conical section having a surface corresponding to the surface of the first frusto-conical section and at least one airflow aperture in the corresponding surface;
        the second frusto-conical section being rotatable with respect to the first frusto-conical section to a first position at which the at least one airflow aperture of the first frusto-conical section is aligned with the at least one airflow aperture of the second frusto-conical section to permit air to flow through the second end.

2. The combination of claim 1, wherein the interface device acts between the inlet port and the end to retain the end at the inlet port.

3. The combination of claim 1, wherein the second frusto-conical section is rotatable with respect to the first frusto-conical section to a second position at which at least one airflow aperture of the first frusto-conical section is blocked by the surface of the second frusto-conical section and the at least one airflow aperture of the second frusto-conical section is blocked by the surface of the first frusto-conical section to prevent air flowing through the end.

4. The combination of claim 3, wherein the second frusto-conical section is received within the first frusto-conical section.

5. A convective system for controlling the temperature of a person, comprising:
    a convective warming device with an inlet port including a generally planar sheet of flexible material with a port opening;
    a blower for providing pressurized, thermally regulated air;
    an air hose with a first end receivable by the blower and a second end receivable by the inlet port;
    an interface device to restrict airflow from the second end in response to separation of the second end from the inlet port;
    wherein the interface device includes:
        a first frusto-conical section received on the second end, the first frusto-conical section including a surface with at least one airflow aperture; and,
        a second frusto-conical section received on the first frusto-conical section, the second frusto-conical section having a surface corresponding to the surface of the first frusto-conical section and at least one airflow aperture in the corresponding surface;
        the second frusto-conical section is rotatable with respect to the first frusto-conical section to a position at which the at least one airflow aperture of the first frusto-conical section is aligned with the at least one airflow aperture of the second frusto-conical section to permit air to flow through the second end.

6. The convective system of claim 5, wherein the interface device acts between the inlet port and the second end to keep the second end open when the second end is received by the inlet port.

7. The convective system of claim 5, wherein the second frusto-conical section is rotatable with respect to the first frusto-conical section to a position at which at least one airflow aperture of the first frusto-conical section is blocked by the surface of the second frusto-conical section and the at least one airflow aperture of the second frusto-conical section is blocked by the surface of the first frusto-conical section to prevent air flowing through the second end.

8. The convective system of claim 7, wherein the second frusto-conical section is received within the first frusto-conical section.

9. The convective system of claim 5, wherein the convective warming device is an inflatable convective warming device.

10. A combination for controlling airflow through an air hose, comprising:
    an inlet port including a generally planar sheet of flexible material with a port opening for receiving an end of an air hose to receive air flow from the end; and,
    an interface device acting at the end which is moveable between a first configuration permitting airflow through the end and a second configuration restricting airflow through the end;
    the interface device including:
        a first frusto-conical section received on the end, the first frusto-conical section including a surface with at least one airflow aperture; and,
        a second frusto-conical section received on the first frusto-conical section, the second frusto-conical section having a surface corresponding to the surface of the first frusto-conical section and at least one airflow aperture in the corresponding surface;
        the second frusto-conical section is rotatable with respect to the first frusto-conical section to a first position at which the at least one airflow aperture of the first frusto-conical section is aligned with the at least one airflow aperture of the second frusto-conical section to permit air to flow through the second end.

11. The combination of claim 10, wherein the interface device acts between the inlet port and the end to keep the end in the first configuration when the end is received by the inlet port.

12. The combination of claim 10, wherein the second frusto-conical section is rotatable with respect to the first frusto-conical section to a second position at which at least one airflow aperture of the first frusto-conical section is blocked by the surface of the second frusto-conical section and the at least one airflow aperture of the second frusto-conical section is blocked by the surface of the first frusto-conical section to prevent air flowing through the end.

13. The combination of claim 12, wherein the second frusto-conical section is received within the first frusto-conical section.

* * * * *

UNITED STATES PATENT AND TRADEMARK OFFICE
CERTIFICATE OF CORRECTION

PATENT NO. : 7,338,515 B2
APPLICATION NO. : 10/131068
DATED : March 4, 2008
INVENTOR(S) : Van Duren et al.

It is certified that error appears in the above-identified patent and that said Letters Patent is hereby corrected as shown below:

<u>Column 3, line 24</u>
Delete the word "of".

<u>Column 3, line 28</u>
Delete the word "warning" and replace it with "warming".

<u>Column 3, line 46</u>
Delete the word "an" and replace it with the word "a".

<u>Column 3, line 55</u>
Delete the word "an" and replace it with the word "a".

<u>Column 3, line 60</u>
Delete the word "an" and replace it with the word "a".

<u>Column 4, line 2</u>
Delete the word "bums" and replace it with the word "burns".

<u>Column 4, line 17</u>
Delete the word "In" and replace it with the word "in".

<u>Column 4, line 18</u>
Delete "6,477,538both" and replace it with "6,477,538, both"

<u>Column 4, line 19</u>
Delete "Incorporated" and replace it with "incorporated".

<u>Column 4, line 21</u>
Delete "Implicate" and replace it with "implicate".

<u>Column 4, line 65</u>
Delete the letter "e" and replace it with the word "be".

<u>Column 8, line 64</u>
Delete the word "In" and replace it with the word "in".

CERTIFICATE OF CORRECTION (continued)
U.S. Pat. No. 7,338,515 B2

<u>Column 9, line 22</u>
After the word "blocked" add ".".

<u>Column 13, line 12</u>
After "7B" add ",".

Signed and Sealed this

Nineteenth Day of January, 2010

David J. Kappos
*Director of the United States Patent and Trademark Office*